(12) United States Patent
Gao et al.

(10) Patent No.: US 12,162,866 B1
(45) Date of Patent: Dec. 10, 2024

(54) CRYSTAL FORM OF PYRAZOLYL-AMINO-PYRIMIDINYL DERIVATIVE, AND PREPARATION METHOD THEREFOR AND USE THEREOF

(71) Applicant: LYNK PHARMACEUTICALS CO., LTD., Zhejiang (CN)

(72) Inventors: Yujun Gao, Hangzhou (CN); Jian Wu, Hangzhou (CN); Xiaodong Li, Hangzhou (CN); Michael Lawrence Vazquez, Hangzhou (CN); Zhaokui Wan, Hangzhou (CN)

(73) Assignee: LYNK PHARMACEUTICALS CO., LTD., Zhejiang (CN)

( * ) Notice: Subject to any disclaimer, the term of this patent is extended or adjusted under 35 U.S.C. 154(b) by 0 days.

(21) Appl. No.: 18/495,213

(22) Filed: Oct. 26, 2023

Related U.S. Application Data

(63) Continuation of application No. PCT/CN2023/095378, filed on May 19, 2023.

(51) Int. Cl.
C07D 405/14 (2006.01)
A61K 31/277 (2006.01)
C07D 413/00 (2006.01)

(52) U.S. Cl.
CPC .......... *C07D 405/14* (2013.01); *A61K 31/277* (2013.01); *C07B 2200/13* (2013.01); *C07D 413/00* (2013.01)

(58) Field of Classification Search
CPC .. C07D 405/14; C07D 413/00; A61K 31/277; C07B 2200/13
See application file for complete search history.

(56) References Cited

U.S. PATENT DOCUMENTS

2022/0298144 A1   9/2022   Wan et al.

FOREIGN PATENT DOCUMENTS

| CN | 103298794 A | 9/2013 |
|---|---|---|
| CN | 113227074 A | 8/2021 |

(Continued)

OTHER PUBLICATIONS

Jul. 19, 2023 International Search Report issued in International Patent Application No. PCT/CN2023/095378.

(Continued)

*Primary Examiner* — Alicia L Otton
*Assistant Examiner* — David M Shim
(74) *Attorney, Agent, or Firm* — Harness, Dickey & Pierce, P.L.C.

(57) ABSTRACT

Provided in the present disclosure is crystal form I of compound 1, and a preparation method thereof and the use thereof.

13 Claims, 19 Drawing Sheets

(56) References Cited

FOREIGN PATENT DOCUMENTS

| WO | WO-2012062704 A1 | 5/2012 | |
| WO | WO 2020/119819 A1 * | 6/2020 | ........... C07D 403/12 |

OTHER PUBLICATIONS

Jul. 19, 2023 Written Opinion of the International Searching Authority issued in International Patent Application No. PCT/CN2023/095378.

* cited by examiner

CRYSTAL FORM OF PYRAZOLYL-AMINO-PYRIMIDINYL DERIVATIVE, AND PREPARATION METHOD THEREFOR AND USE THEREOF

CROSS-REFERENCE TO RELATED APPLICATIONS

The present application is a continuation application of International Application No. PCT/CN2023/095378, filed on May 19, 2023.

TECHNICAL FIELD

The present disclosure relates to a crystal form of a pyrazolyl-amino-pyrimidinyl derivative, and a preparation method therefor and the use thereof.

BACKGROUND

The JAK-STAT pathway mediates intracellular signaling of a variety of cytokines in the body. Early studies have shown that there are elevated levels of a variety of inflammatory cytokines in the skin lesions of AD patients, such as Th1 (γ-interferon), Th2 (IL-4, IL-13 and IL-31) and Th22 (IL-22) cytokines, suggesting that AD pathogenesis is closely related to the JAK-STAT pathway. The binding of IL-4 to IL-4 receptors α and γ, and the binding of IL-13 to IL-13 receptor al can activate JAK1/3, thereby promoting STAT3/6 phosphorylation. STAT3 can disrupt skin barrier integrity by down-regulating proteins related to KC differentiation; STAT6 can up-regulate chemokines involved in AD pathogenesis, and the differentiation of Th0 cells into Th2 cells through JAK1/3-STAT6 pathway causes AD pathogenesis. Eosinophils are one of the most important effector cells of AD. A complex of IL-5 and its receptor β chain is involved in the process of regulating the proliferation, survival and efficacy of eosinophils through the JAK2-STAT1/5 pathway. Activated eosinophils are attracted to the skin by chemokines released by epidermal cells in a high Th2 immune environment that are involved in AD pathogenesis, further aggravating the AD condition.

Among JAK inhibitors currently under development, Delgocitinib (marketed) by Japan Tobacco, Ruxolitinib (marketed) by Incyte, and Tofacitinib (phase II) by Pfizer have advanced rapidly. The results show that Delgocitinib significantly improves the clinical score of patients in the phase III clinical study on the treatment of AD; the results of the phase II and phase III studies on the treatment of AD with Ruxolitinib show that the drug has rapid antipruritic and anti-inflammatory effects and is well tolerated; in the phase II study on Tofacitinib, the EASI score of AD patients is significantly improved after treatment with 2% ointment for 4 weeks, with good local tolerance and safety. In addition, JAK inhibitors under development for the treatment of AD in China, including Jaktinib Hydrochloride Cream by Suzhou Zelgen Biopharmaceuticals Co., Ltd. and SHR0302 Base Ointment by Jiangsu Hengrui Medicine Co., Ltd., have also entered phase I/II and phase II/III, respectively. However, the current local treatment of AD still cannot meet the clinical requirements. The continuous development of safer and more effective JAK inhibitors can improve the current situation of insufficient treatment drugs, improve the therapeutic effect and quality of life of patients with atopic dermatitis, and have great significance and market prospects.

It has been found from the preclinical study that LNK01004 (having a structure as shown below) is a pan-Janus kinase (JAK) inhibitor, has a strong inhibitory effect on JAK1, JAK2 and TYK2, and can inhibit p-STAT signaling pathway induced by multiple cytokines in vivo and in vitro. In vivo and in vitro experimental results show that LNK01004 can not only inhibit p-STAT signaling pathway induced by cytokines in immune cells, but also effectively inhibit p-STAT signaling pathway induced by cytokines related to psoriasis or atopic dermatitis in skin tissues via skin application. Unlike Ruxolitinib and Tofacitinib, LNK01004 can also inhibit the proliferation of keratinocytes.

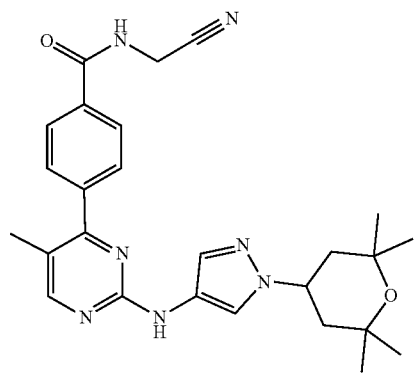

BRIEF SUMMARY

The present disclosure provides a crystal form of a pyrazolyl-amino-pyrimidinyl derivative, and a preparation method therefor and the use thereof. The crystal form meets one or more of the following effect advantages: good physical and chemical properties, solid state stability, good solubility, low hygroscopicity, and good processability of the preparation process.

The present disclosure provides a crystal form I of compound 1, wherein

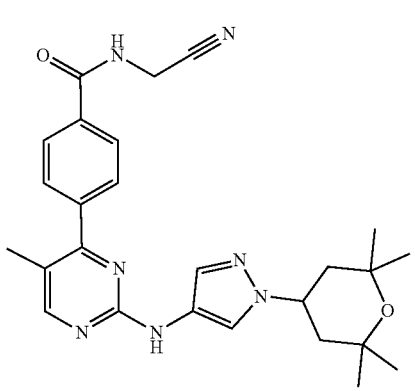

the crystal form I has an X-ray powder diffraction pattern comprising diffraction peaks at the following positions: 8.60°±0.2°, 10.25°±0.2°, 11.96°±0.2°, 14.35°±0.2°, 15.39°-0.2°, 16.59°±0.2°, 17.06°±0.2°, and 18.16°±0.2° 2θ, as determined by using Cu—Kα radiation.

In a certain embodiment, the crystal form I has an X-ray powder diffraction pattern further comprising diffraction peaks at one or more of the following positions: 12.77°±0.2°, 13.48°±0.2°, 14.04°±0.2°, 17.27°±0.2°, 18.83°±0.2°, 20.52°±0.2°, 20.77°±0.2°, 21.45°±0.2°, 22.12°±0.2°, 22.79°±0.2°, 23.55°±0.2°, 24.04°±0.2°, 24.40°±0.2°, 25.08°±0.2°, 25.87°±0.2°, 26.51°±0.2°, 26.73°±0.2°, 26.89°±0.2°, 27.36°±0.2°, and 28.29°±0.2° 2θ.

In a certain embodiment, the crystal form I has an X-ray powder diffraction pattern further comprising diffraction peaks at one or more of the following positions: 28.93±0.2°, 29.42°±0.2°, 30.63°±0.2°, 33.00°±0.2°, 33.37°±0.2°, 34.43°±0.2°, and 37.09°±0.2° 2θ.

In a certain embodiment, the crystal form I has an X-ray powder diffraction pattern at 2θ comprising diffraction peaks as shown in the table below:

| Diffraction angle [° 2θ] | d value [Å] | Relative intensity [%] |
|---|---|---|
| 8.599 | 10.27532 | 94.0 |
| 10.250 | 8.62286 | 41.5 |
| 11.957 | 7.39559 | 80.8 |
| 12.774 | 6.92428 | 14.1 |
| 13.482 | 6.56235 | 13.1 |
| 14.043 | 6.30159 | 52.8 |
| 14.345 | 6.16938 | 33.9 |
| 15.392 | 5.75198 | 16.1 |
| 16.594 | 5.33787 | 18.7 |
| 17.063 | 5.19224 | 56.9 |
| 17.270 | 5.13049 | 27.3 |
| 18.156 | 4.88225 | 100.0 |
| 18.830 | 4.70888 | 6.0 |
| 20.523 | 4.32402 | 26.0 |
| 20.765 | 4.27428 | 10.0 |
| 21.446 | 4.14001 | 43.6 |
| 22.118 | 4.01569 | 17.0 |
| 22.792 | 3.89842 | 5.7 |
| 23.545 | 3.77553 | 10.5 |
| 24.043 | 3.69847 | 13.5 |
| 24.406 | 3.64422 | 33.5 |
| 25.081 | 3.54761 | 20.4 |
| 25.868 | 3.44150 | 2.8 |
| 26.508 | 3.35979 | 2.8 |
| 26.732 | 3.33219 | 5.4 |
| 26.889 | 3.31302 | 9.2 |
| 27.360 | 3.25704 | 10.2 |
| 28.285 | 3.15261 | 6.9 |
| 28.930 | 3.08383 | 30.2 |
| 29.419 | 3.03366 | 5.0 |
| 30.630 | 2.91642 | 3.4 |
| 33.000 | 2.71216 | 3.7 |
| 33.370 | 2.68298 | 2.6 |
| 34.429 | 2.60282 | 2.2 |
| 37.089 | 2.42198 | 2.0 |

In a certain embodiment, the crystal form I has an X-ray powder diffraction pattern at 2θ substantially as shown in FIG. 1.

In a certain embodiment, the crystal form I has a differential scanning calorimetry pattern comprising an endothermic peak at 207.4° C. to 209.2° C.

In a certain embodiment, the crystal form I has a differential scanning calorimetry pattern comprising an endothermic peak at 207.4° C. to 209.2° C., with a heat of fusion of 123.76 J/g.

In a certain embodiment, the crystal form I has a differential scanning calorimetry pattern substantially as shown in FIG. 2.

In a certain embodiment, the crystal form I has a thermogravimetric analysis pattern comprising a weight loss of 0.0% at 30.07° C. to 208.96° C., indicating that the crystal form I is an anhydrous compound.

In a certain embodiment, the crystal form I has a thermogravimetric analysis pattern substantially as shown in FIG. 3.

The present disclosure also provides a method for preparing the above-mentioned crystal form I, comprising scheme 1 or scheme 2, wherein the scheme 1 comprises the step of subjecting a solution of the compound 1 in methanol to crystallization to obtain the crystal form I;

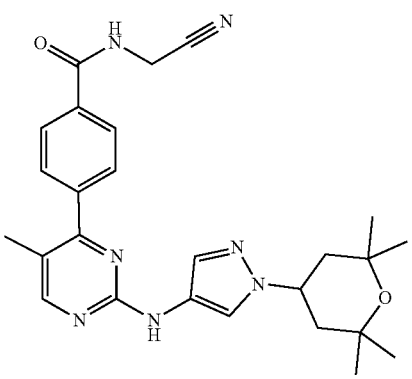

the scheme 2 comprises the step of cooling a solution of the compound 1 in tetrahydrofuran/methanol and isopropanol to obtain the crystal form I.

In a certain embodiment, in the scheme 1, during the crystallization, the mass ratio of the solution to the compound 1 is (1:6) to (1:8.5), preferably (1:6.3) to (1:8.3).

In a certain embodiment, the scheme 1 preferably comprises the following operations: at 40° C., adding methanol to a solution of the compound 1 and tetrahydrofuran, performing concentration, adding methanol again to a concentrated solution, and stirring for crystallization to obtain the crystal form I, wherein the temperature at which the compound 1 is dissolved in the tetrahydrofuran to form the solution is preferably 50° C. to 60° C.;

the mass ratio of the compound 1 to the tetrahydrofuran is preferably (1:8) to (1:9), more preferably 1:8.7;

the mass ratio of the compound 1 to the methanol added for the first time is preferably (1:16) to (1:18), more preferably 1:17;

the mass of the concentrated solution is preferably 4 to 6 times the mass of the compound 1, more preferably 5 times;

the mass ratio of the compound 1 to the methanol added for the second time is preferably (1:2) to (1:3), more preferably 1:2.3.

In a certain embodiment, the scheme 1 may further comprise the following post-processing steps: filtering, washing, drying under reduced pressure, and sieving to obtain the crystal form I.

In a certain embodiment, in the scheme 2, the mass ratio of the compound 1 to tetrahydrofuran/methanol is (1:3) to (1:5), preferably 1:4.

In a certain embodiment, in the scheme 2, in the tetrahydrofuran/methanol, the mass ratio of tetrahydrofuran to methanol is (2:1) to (1:2), preferably 1:1.

In a certain embodiment, in the scheme 2, the mass ratio of the compound 1 to isopropanol is (1:11) to (1:13), preferably 1:12.

In a certain embodiment, in the scheme 2, the temperature at which the compound 1 is dissolved in tetrahydrofuran/methanol and isopropanol is 50° C. to 60° C., preferably 55° C.

In a certain embodiment, in the scheme 2, the cooling is to lower the temperature to 0° C. to 5° C., preferably to 0° C.

In a certain embodiment, in the scheme 2, the temperature-holding time after the cooling is related to the reaction scale, and generally the time point at which the product no longer increases is taken as the reaction end point; the temperature-holding time is preferably 15 h to 30 h, more preferably 24 h.

In a certain embodiment, the scheme 2 preferably comprises the following operations: warming the compound 1 and tetrahydrofuran/methanol, adding isopropanol to dissolve the sample, adding isopropanol again, and cooling to form a suspension to obtain the crystal form I.

In a certain embodiment, the scheme 2 may further comprise the following post-processing steps: filtering, washing, drying under reduced pressure, and sieving to obtain the crystal form I.

The present disclosure also provides a pharmaceutical composition, comprising the above-mentioned crystal form I and a pharmaceutical excipient.

The present disclosure also provides the use of the above-mentioned crystal form I in the preparation of a drug for treating and/or preventing a disease related to JAK kinases.

In a certain embodiment, the disease related to JAK kinases is inflammatory bowel disease, psoriasis, vitiligo, atopic dermatitis, systemic lupus erythematosus, asthma, diabetic nephropathy, chronic myelogenous leukemia (CML), essential thrombocythemia (ET), polycythemia vera (PV), myelofibrosis (MF), breast cancer or ovarian cancer.

On the basis of not departing from common knowledge in the art, the above-mentioned various preferred conditions can be combined in any manner, such that various preferred examples of the present disclosure are obtained.

Reagents and raw materials used in the present disclosure are all commercially available.

The positive effects of the present disclosure lie in: the crystal form I has good physical and chemical properties, good high-temperature (such as 60° C.) and high-humidity (92.5% RH) stability, high-pressure (10 Mpa) solid state stability, good solubility (far greater than 8 µg/mL), low hygroscopicity, uniform particle size distribution, good solid morphology, processability of the preparation process, and good development prospects.

DETAILED DESCRIPTION

Figure 1:
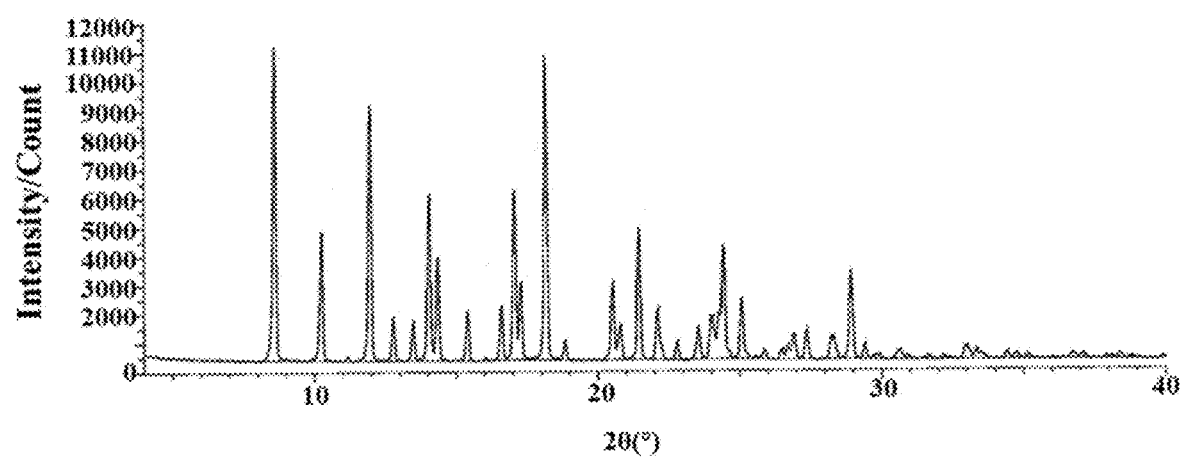
FIG. 1 is an XRPD pattern of the crystal form I.

The present disclosure is further described below by way of examples; however, the present disclosure is not limited to the scope of the described examples. For the experimental methods in which no specific conditions are specified in the following examples, selections are made according to conventional methods and conditions or according to the product instructions.

XRPD Analysis Method

| 1. Test preparation | | |
|---|---|---|
| Category | Name | Remark |
| Instrument | Bruker D8 Advance X-ray diffractometer | Or equivalent instrument |
| Material | Monocrystalline silicon plate | Or equivalent plate |

| 2. Parameter setting | | |
|---|---|---|
| Parameter | | Setting |
| Generator | Light pipe | Cu:K-Alpha1 ($\lambda$ = 1.54060 Å) |
| | Voltage | 40 KV |
| | Current | 40 mA |
| Optical path | Front Soller | 2.5 deg |
| | Secondary Soller | 2.5 deg |
| | Divergence | 0.60 mm |
| | Mode | Fixed |
| Detector | Mode | Lynxeye (1D mode) |
| | PSD development angle | 2.1° |
| Scanning parameter | Type | Coupled Two Theta/Theta |
| | Mode | Continuous PSD fast |
| | Range | 4 to 40 deg |
| | Step size | 0.02 deg |
| | Step length | 0.12 s |

Remark: the above parameters are established according to Bruker D8 XRPD and can be adjusted according to different instruments.

3. Test and Result Report

An appropriate amount of a sample (e.g., 20 to 50 mg, adjustable) was loaded onto a monocrystalline silicon plate, and uniformly coated on the central area of the monocrystalline silicon plate, as shown in the figure below. If the sample has larger particles, a back-loaded sample plate may be used. When there is no requirement for response intensity, both flat and grooved monocrystalline silicon plates may be used; otherwise, a grooved monocrystalline silicon plate should be used to keep the loading height consistent.

If necessary, a thin layer of vaseline or silicone oil may be coated on the surface of a monocrystalline silicon plate to attach the sample, and the excess sample is gently tapped off. The sample plate was loaded onto the sample holder of the XRPD and scanned, to acquire the pattern, and the results were reported.

DSC Test Method

| 1. Test preparation | | |
|---|---|---|
| Category | Name | Backup control |
| Instrument | Differential scanning calorimeter | TA Discovery series or equivalent instrument |
| | Analytical balance | Precision: at least 1 mg |
| Material | Crucible tray | Low-Mass aluminum tray, Tzero or equivalent |
| | Cover | Aluminium, Tzero or equivalent |

| 2. Parameter setting | |
|---|---|
| Parameter | Setting |
| Flow rate of nitrogen | 50 ml/min |
| Data acquisition frequency | 1.00 s/pt |
| Range of temperature rise | Room temperature to 300° C. |
| Rate of temperature rise | 10° C./min |

3. Test and Result Report

An appropriate amount of a sample (not too full to prevent overflow during heating) was taken and placed in a crucible tray, covered with a cover, and sealed with a cover pressing device. An empty crucible tray was taken as a blank control. The crucible tray and cover used for the blank control should be identical to those used for the sample. The crucible trays were mounted on the corresponding sample holders: the sample crucible tray was placed on the sample holder, and the blank crucible tray was placed on the control holder. A method was selected, and a workstation software was used for data processing. The results were reported.

TGA Test Method

| 1. Test preparation | | |
|---|---|---|
| Category | Name | Remark |
| Instrument | Thermogravimetric analyzer | TA TGA55/GA550 or equivalent instruments |
| Material | Sample tray | Alumina or platinum material |

| 2. Parameter setting | |
|---|---|
| Parameter | Setting |
| Flow rate of purge gas for balance | 40 ml/min |
| Flow rate of purge gas for furnace | 10 ml/min |
| Range of temperature rise | Room temperature to 300° C. |
| Rate of temperature rise | 10° C./min |

3. Test and Result Report

An empty sample tray was placed in a target position on Auto Sampler, "TARE" on the workstation was clicked, and then the instrument would automatically weigh the tray, and remove the tare weight after the furnace was closed. About 2 to 10 mg of a sample was weighed precisely and placed in the sample tray with the tare weight removed. The sample information was edited, and a method was selected. Sample analysis was started when "Sta" was clicked, and a curve of sample weight percentage changing with temperature was automatically recorded by the workstation. "Analysis" was clicked; "Weight change" in the drop-down menu was selected; "Analyze" was clicked to perform analyze command; the weight loss percentage (%) of the sample was automatically calculated by the workstation; and the results were reported.

PLM (Polarized Light Microscopy) Test Method

| 1. Test preparation | |
|---|---|
| Category | Name |
| Instrument | Nikon LV100POL polarizing microscope |
| Material | Glass slide/cover glass |

2. Test and Result Report

Several particles of a sample were placed in mineral oil (e.g., silicone oil) to form a suspended matter, which was then placed on a clean glass slide. An appropriate amount of the suspension was placed on a glass slide and covered with a cover glass. For particles with irregular shapes, the characterization of particle size must also include particle information. The homogeneity of the powder should be checked using appropriate magnification. The results of the microphotographs were reported.

Crystal Form I Preparation and Characterization

Example 1

LNK01004 (as an amorphous form, prepared with reference to example 113 of CN 113227074 A) (net content: 1.73 kg, 1.00±0.02×) and tetrahydrofuran (15 kg, 8.7×) were added to reactor R1, heated to 50° C. to 60° C., and stirred for 1 to 3 h until completely dissolved.

The temperature was controlled to be 40° C., and methanol (30 kg, 17×) was then added. The mixture was concentrated under reduced pressure to 4.0 to 6.0×, added with methanol (4 kg, 2.3×) again, and stirred for 1 to 3 h.

The suspension was filtered, and the filter cake was washed by adding methanol (2 kg, 1.2×). At 40° C. to 50° C., the filter cake was dried under reduced pressure until the moisture and solvent residue were qualified (tetrahydrofuran≤720 ppm, and methanol≤5000 ppm). After dried to be qualified, the resulting material was sieved to obtain 1.362 kg of a crystal form I (JR-C200212007-FPF21001) of the final product LNK01004, with an XRPD pattern as shown in FIG. 1, a purity of 99.91%, and a yield of 90%.

| XRPD data of JR-C200212007-FPF21001 | | |
|---|---|---|
| Diffraction angle [° 2θ] | d value [Å] | Relative intensity [%] |
| 8.599 | 10.27532 | 94.0 |
| 10.250 | 8.62286 | 41.5 |
| 11.957 | 7.39559 | 80.8 |
| 12.774 | 6.92428 | 14.1 |
| 13.482 | 6.56235 | 13.1 |
| 14.043 | 6.30159 | 52.8 |
| 14.345 | 6.16938 | 33.9 |
| 15.392 | 5.75198 | 16.1 |
| 16.594 | 5.33787 | 18.7 |
| 17.063 | 5.19224 | 56.9 |
| 17.270 | 5.13049 | 27.3 |
| 18.156 | 4.88225 | 100.0 |
| 18.830 | 4.70888 | 6.0 |
| 20.523 | 4.32402 | 26.0 |
| 20.765 | 4.27428 | 10.0 |
| 21.446 | 4.14001 | 43.6 |
| 22.118 | 4.01569 | 17.0 |
| 22.792 | 3.89842 | 5.7 |

-continued

XRPD data of JR-C200212007-FPF21001

| Diffraction angle [° 2θ] | d value [Å] | Relative intensity [%] |
|---|---|---|
| 23.545 | 3.77553 | 10.5 |
| 24.043 | 3.69847 | 13.5 |
| 24.406 | 3.64422 | 33.5 |
| 25.081 | 3.54761 | 20.4 |
| 25.868 | 3.44150 | 2.8 |
| 26.508 | 3.35979 | 2.8 |
| 26.732 | 3.33219 | 5.4 |
| 26.889 | 3.31302 | 9.2 |
| 27.360 | 3.25704 | 10.2 |
| 28.285 | 3.15261 | 6.9 |
| 28.930 | 3.08383 | 30.2 |
| 29.419 | 3.03366 | 5.0 |
| 30.630 | 2.91642 | 3.4 |
| 33.000 | 2.71216 | 3.7 |
| 33.370 | 2.68298 | 2.6 |
| 34.429 | 2.60282 | 2.2 |
| 37.089 | 2.42198 | 2.0 |

Characterization of Crystal Form I

The acquired typical characterization data of the crystal form I obtained from JR-C200212007-FPF21001 are as shown below. The characterization data show that the crystal form I is a stable solvent-free crystal, which can obtain very high purity, stable melting point, solvent-free encapsulation, and good morphology and particle size distribution, and has no obvious hygroscopicity, and these characteristics are beneficial to the subsequent development and production of bulk API and preparations.

Characterization data of crystal form I

Sample number: JR-C200212007-FPF21001

Figure 2:
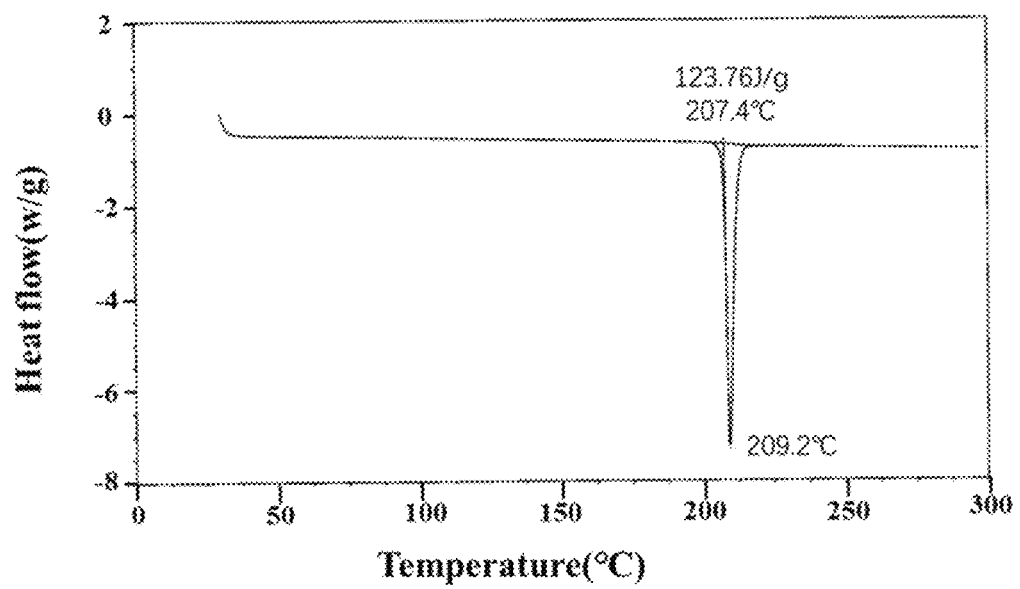
FIG. 2 is a DSC pattern of the crystal form I.
Figure 4:
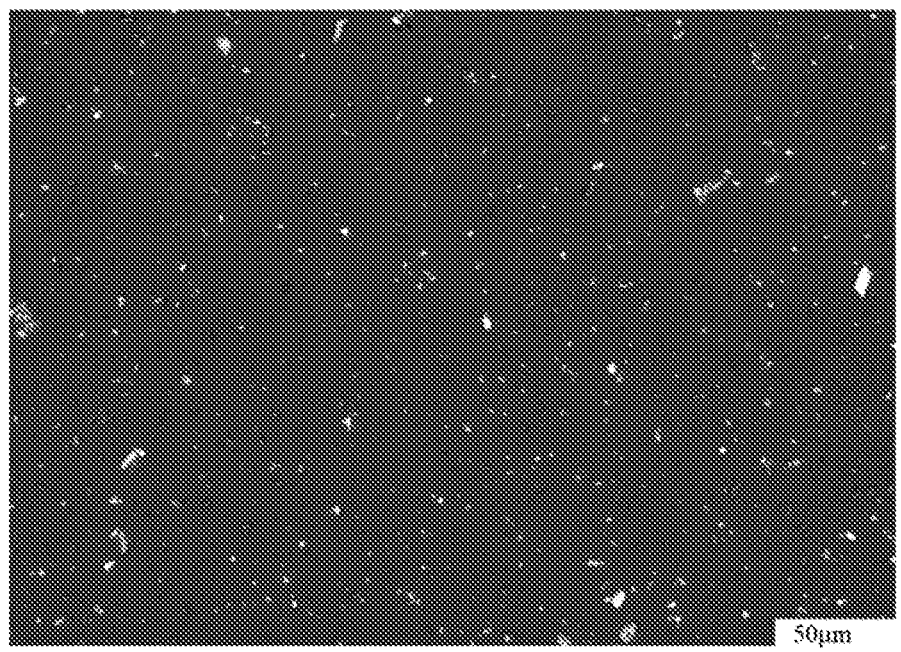
FIG. 4 is a PLM pattern of the crystal form I.
Figure 5:
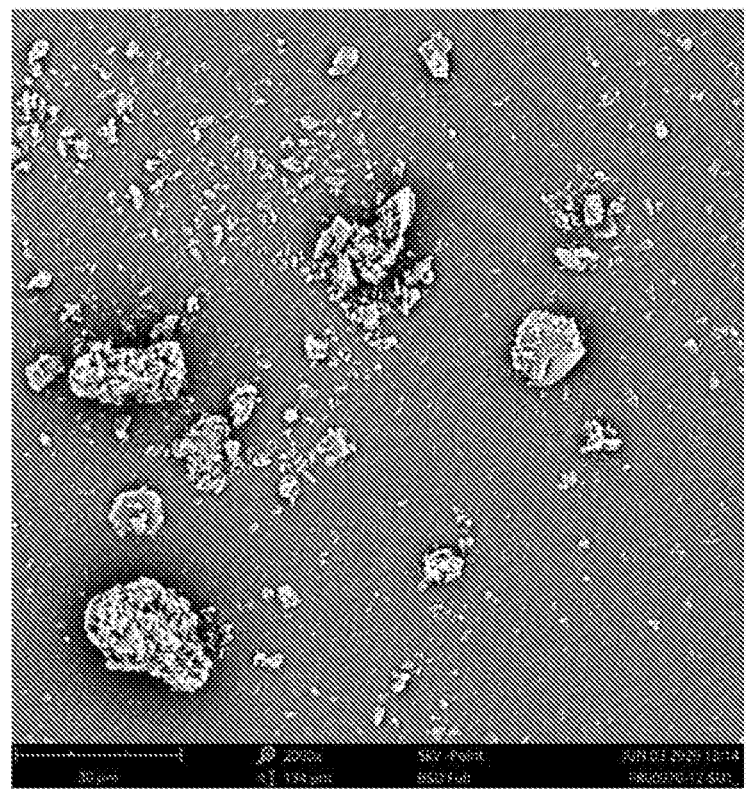
FIG. 5 is an SEM pattern of the crystal form I.
Figure 6:
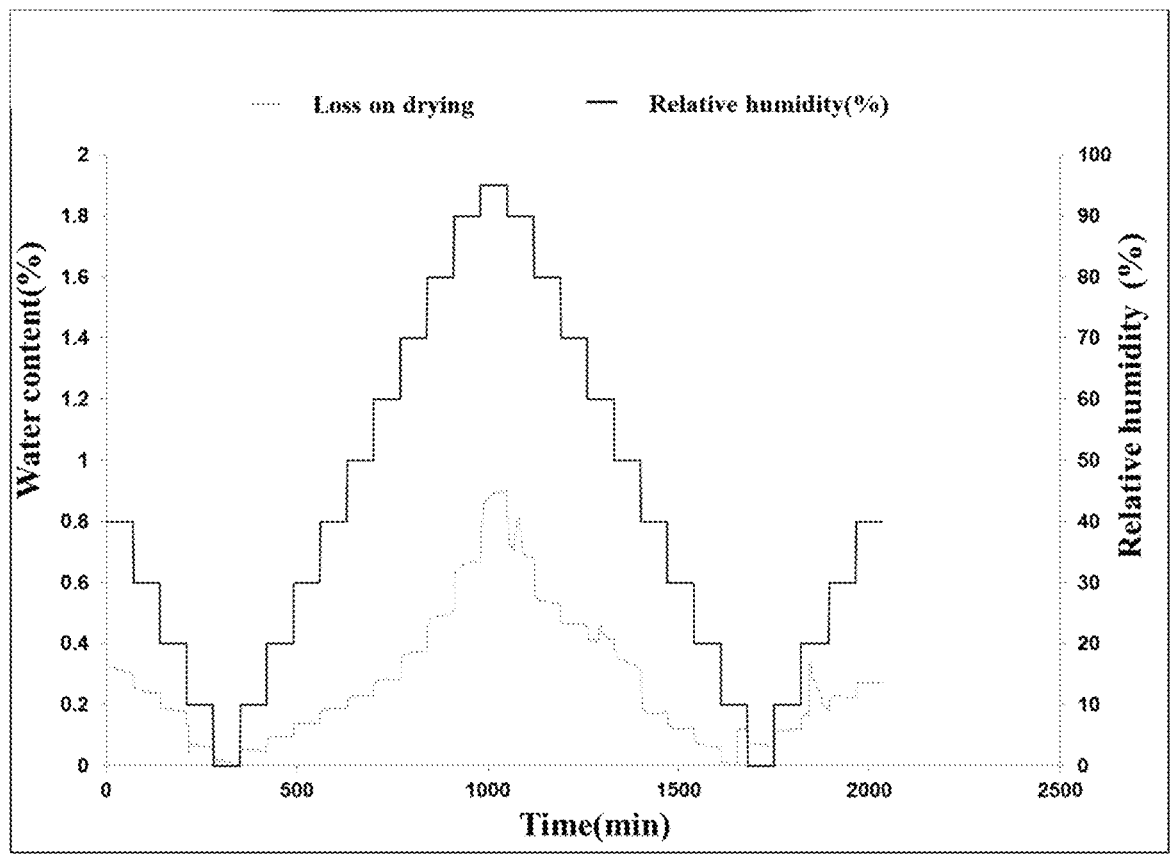
FIG. 6 is a DVS pattern of the crystal form I.
Figure 6B:
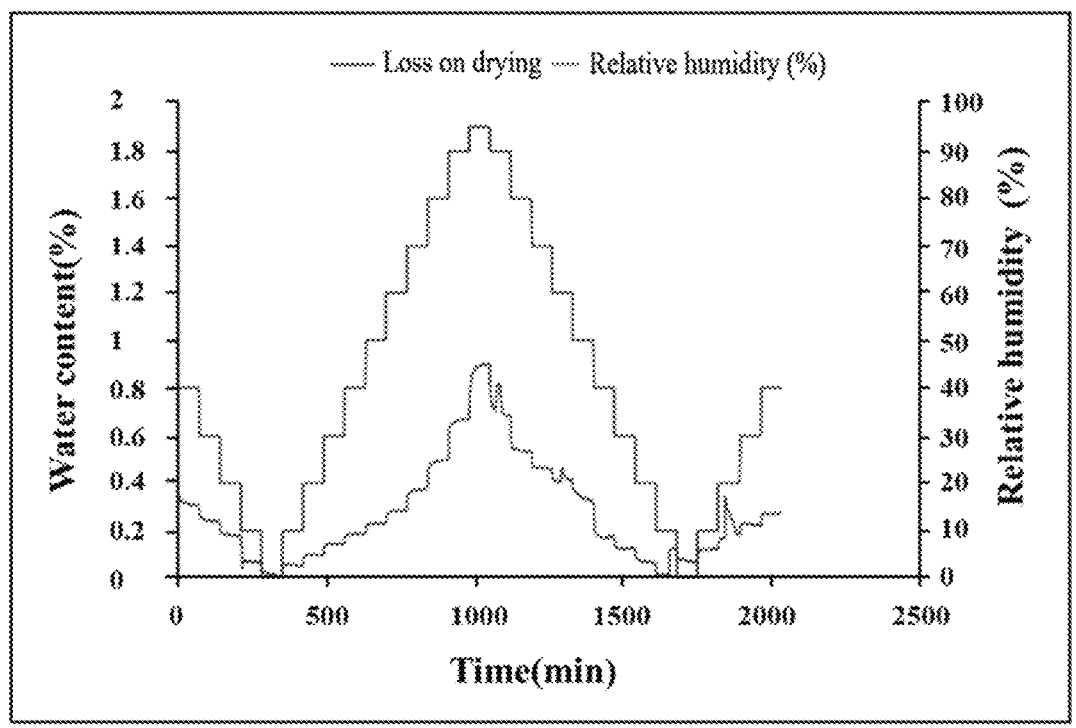
Figure 7:
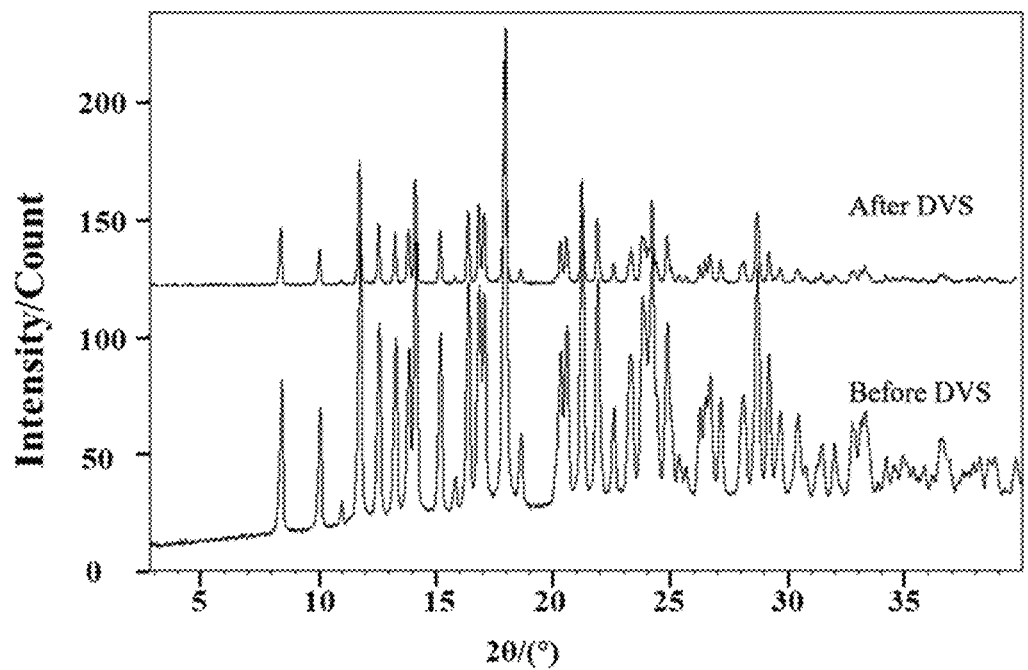
FIG. 7 is an XRPD pattern of the crystal form I before and after DVS testing.

| Parameter | Method | Result |
|---|---|---|
| Purity | HPLC | 99.91% |
| Melting point | DSC (FIG. 2), 10° C./min | 207.4° C. to 209.2° C.; 123.76 J/g |
| X-ray diffraction | 3° to 40° (2 theta) | High crystallinity |
| Thermal weight loss | TGA, 10° C./min (FIG. 3) | Weight loss of 0.0% from 30.07° C. to 208.96° C. |
| Solvent residue | $^1$H-NMR | None |
| Water content | Karl Fisher | 0.1% |
| Morphology | PLM (FIG. 4) | Blocky |
| Morphology | SEM (FIG. 5) | Blocky |
| Particle size distribution | PSD dry method | D10 = 6 μm; D50 = 14 μm; D90 = 31 μm |
| Hygroscopicity | DVS (FIG. 6) | Weight gain of 0.9% under 95% RH. No crystal form transformation after completion of DVS characterization (FIG. 7) |

Crystal Form I Preparation Example 2

LNK01004 (as an amorphous form, prepared with reference to example 113 of CN 113227074 A) (net content: 5 kg, 1.00±0.02×) and tetrahydrofuran/methanol in 1:1 (20 kg, 4.0×) were added to reactor R1 and heated to 50° C. to 60° C.; isopropanol (5 kg, 1.0×) was added; and the mixture was stirred for 1 to 3 h until completely dissolved.

Isopropanol (55 kg, 11.0×) was added while controlling the temperature at 55° C. for 1 to 3 h.

The reaction temperature was lowered to 0° C. within 5.0 h. The temperature was kept at 0° C. for 24 h to form a suspension.

The suspension was filtered, and the filter cake was washed by adding isopropanol (10 kg, 2.0×).

At 40° C. to 50° C., the filter cake was dried under reduced pressure until the moisture and solvent residue were qualified (tetrahydrofuran≤720 ppm, methanol≤5000 ppm, and isopropanol≤5000 ppm). After dried to be qualified, the resulting material was sieved to obtain 4.7 kg of a crystal form I (the characterization data of which were consistent with those of Crystal form I Preparation example 1) of the final product LNK01004, with a purity of 100.0% and a yield of 94%.

Crystal Form I Effect Example 1

1. Water Activity Experiment at 25° C.

20 mg of the crystal form I was weighed, added to 1 mL of an acetone/water system having different water activities, and stirred at 25° C. for 10, 12 or 22 days. The resulting solid was filtered and subjected to XRPD characterization.

Water activity experiment at 25° C.

| Experiment number | Solvent | Result Time/day | XRPD |
|---|---|---|---|
| AW1 | Water (a.w. = 1) | 10 | Crystal form I |
| | | 22 | Crystal form I |
| AW9 | Acetone/water (v:v = 36:64) (a.w. = 0.9) | 12 | Crystal form I |
| AW8 | Acetone/water (v:v = 60.4:39.6) (a.w. = 0.8) | 12 | Crystal form I |
| AW7 | Acetone/water (v:v = 75.8:24.2) (a.w. = 0.7) | 12 | Crystal form I |
| AW2 | Acetone/water (91:9, v:v) (a.w. = 0.6) | 10 | Crystal form I |
| | | 22 | Crystal form I |
| AW3 | Acetone/water (94:6, v:v) (a.w. = 0.5) | 10 | Crystal form I |
| | | 22 | Crystal form I |
| AW4 | Acetone/water (97:3, v:v) (a.w. = 0.3) | 10 | Crystal form I |
| | | 22 | Crystal form I |
| AW5 | Acetone/water (99:1, v:v) (a.w. = 0.1) | 10 | Crystal form I |
| | | 22 | Crystal form I |
| AW6 | Acetone (a.w. = 0) | 10 | Crystal form I |
| | | 22 | Crystal form I |

The results of the water activity experiment show that the anhydrous crystal form I stably exists for a long time (up to 22 days) in a wide water activity range (1% to 100%) and is not transformed into a hydrate or other crystal forms, which is beneficial to keeping a stable crystal form after a preparation enters the body, and to having sufficient absorption and exposure after a drug enters the body.

2. Stability Investigation Results

After the crystal form I was placed under the conditions of high temperature of 60° C. and high humidity of 92.5% RH for 30 days, placed under the condition of illumination of 1×ICH (the total illumination was not less than $1.2 \times 10^6$ Lux·hr and the near ultraviolet energy was not less than 200 w·hr/m$^2$), placed under the accelerated condition (40° C.±2° C./75%±5% RH) for 6 months, and stored under the long-term condition (25° C.±2° C./60%±5% RH) for 18 months, the results of appearance, related substances, assay (in terms of water-free and solvent-free basis), moisture, crystal form, content and microbial limit of the crystal form I were not changed.

| | Item | Placement condition | Investigation time | Investigation item | Conclusion on crystal form |
|---|---|---|---|---|---|
| Influencing factor test | High temperature | 60° C. 40° C. | 5 days, 10 days, 30 days | Appearance, related substances, assay (in terms of water-free and solvent-free basis), moisture, crystal form, content | Crystal form I keeps stable |
| | High humidity | 25° C./92.5% RH 25° C./75% RH2 | 5 days, 10 days, 30 days | Appearance, related substances, assay (in terms of water-free and solvent-free basis), moisture, crystal form, content | |
| | Illumination | 1.2 × 10$^6$ Lux · hr, 200 w · hr/m$^2$ | 1 × ICH | Appearance, related substances, assay (in terms of water-free and solvent-free basis), moisture, crystal form, content | |
| | Conclusion | | | The influencing factor test data show that: after the crystal form I was placed under the conditions of high temperature of 60° C. and high humidity of 92.5% RH for 30 days and placed under the condition of illumination of 1 × ICH (the total illumination was not less than 1.2 × 10$^6$ Lux.hr and the near ultraviolet energy was not less than 200 w · hr/m$^2$), the results of all test items meett he corresponding quality standards; the results showed that the crystal form I drug was stable under the conditions of high temperature, high humidity, and illumination. | |
| Accelerated test | | 40° C. ± 2° C./ 75% ± 5% RH | 1 month, 2 months, 3 months and 6 months | Appearance, related substances, assay (in terms of water-free and solvent-free basis), content and moisture; crystal form test added on month 0, month 3 and month 6; and microbial limit test added on month 0 and month 6 | Crystal form I keeps stable |
| | Intermediate condition test | 30° C. ± 2° C./ 65% ± 5% RH | 1 month, 3 months, 6 months, and 9 months 12 months | Appearance, related substances, assay (in terms of water-free and solvent-free basis), content and moisture; and crystal form and microbial limit tests added on month 0 and month 12 | |
| | Long term test | 25° C. ± 2° C./ 60% ± 5% RH | 1 month, 3 months, 6 months, 9 months, 12 months, 18 months and 24 months | Appearance, related substances, assay (in terms of water-free and solvent-free basis), content and moisture; crystal form test added on month 0, month 3, month 6, month 12 and month 24; and microbial limit test added on month 0, month 12 and month 24 | |

| Item | Placement condition | Investigation time | Investigation item | Conclusion on crystal form |
|------|---------------------|--------------------|--------------------|-----------------------------|
| Conclusion | | | After the crystal form I was placed under the accelerated condition (40° C. ± 2° C./75% ± 5% RH) for 6 months the long-term condition and under (25° C. ± 2° C./60% ± 5% RH) for 18 months, the results of appearance, related substances, assay (in terms of water-free and solvent-free basis), moisture, crystal form I, content and microbial limit were not changed. | |

Crystal Form I Effect Example 2: Study on Dynamic Solubility of Crystal Form I

About 20 mg of the crystal form I was weighed and placed in a 40 mL glass bottle; 10 mL of a simulated gastrointestinal fluid was added; and the mixture was stirred at 400 rpm at 37° C. About 1 mL of the suspension was taken at 1 h, 4 h and 24 h, respectively, and centrifuged at 37° C., and the solubility of the crystal form I at each time point was determined. After 24 h, the pH of the suspension was determined. The remaining suspension was centrifuged, and the remaining solid was subjected to XRPD characterization.

Study on dynamic solubility of crystal form I (37° C.)

| Time (h) | Solubility (μg/mL) | pH after 24 h | XRPD |
|----------|--------------------|---------------|------|
| 1 | 97.4 | 2.1 (simulated gastric juice) | Crystal form I |
| 4 | 92.3 | | |
| 24 | 101.6 | | |
| 1 | 100.5 | 6.6 (simulated pre-meal intestinal fluid) | Crystal form I |
| 4 | 111.0 | | |
| 24 | 120.0 | | |
| 1 | 389.4 | 5.1 (simulated postprandial intestinal fluid) | Crystal form I |
| 4 | 473.7 | | |
| 24 | 627.2 | | |

The results show that the crystal form I has good solubility (far greater than 8 μg/mL) in the simulated gastrointestinal fluid, and the stable absorption of a preparation can be kept in the subsequent preparation development and production.

Crystal Form I Effect Example 3: Press Testing of Crystal Form I

About 10 mg of the crystal form I (sample number: FR00970-12-SU1) was weighed and pressed by a hydraulic press at a pressure of 10 MPa for 5 min, and the transformation of the crystal form and the change in the crystallinity were studied by XRPD characterization. The results show that the advantageous crystal form I keeps stable at high pressure (10 Mpa), which is beneficial to the subsequent stable production of preparations.

Study on crystal transformation under pressure

| Pressure | XRPD | Remark |
|----------|------|--------|
| 10 Mpa | Crystal form I | The crystal form is not changed, and the crystallinity is not changed |

Crystal Form I Effect Example 4: Simulated Dry Grinding of Crystal Form I

About 10 mg of the crystal form I (sample number: FR00970-12-SU1) was weighed and ground for 3 min in a mortar, and the transformation of the crystal form and the change in the crystallinity were studied by XRPD characterization. The results show that the crystal form I keeps stability under the dry grinding condition, which is beneficial to the subsequent production of preparations.

Simulated dry grinding experiment

| Investigation method | XRPD | Remark |
|----------------------|------|--------|
| Dry grinding for 3 min | Crystal form I | The crystal form is not changed, and the crystallinity is slightly reduced |

Crystal Form I Effect Example 5: Simulated Dry Grinding of Crystal Form I

About 10 mg of the crystal form I (sample number: FR00970-12-SU1) was weighed; 40 μL of water or ethanol was added; the mixture was ground for 3 min in a mortar; and the transformation of the crystal form and the change in the crystallinity were studied by XRPD characterization. The results show that the advantageous crystal form I keeps stability under the wet grinding condition, which is beneficial to the subsequent production of preparations.

Simulated wet grinding experiment

| Solvent | XRPD | Remark |
|---------|------|--------|
| Ethanol | Crystal form I | The crystal form is not changed, and the crystallinity is slightly reduced |
| Water | Crystal form I | The crystal form is not changed, and the crystallinity is slightly reduced |

Crystal Form I Effect Example 6:
Pharmacodynamic Data of Crystal Form I

In this test, a migration detection technology was used to detect the half maximal inhibitory concentrations (IC50) of the crystal form I of compound LNK01004, Ruxolitinib, Tofacitinib and Upadacitinib on activities of JAK1, JAK2, JAK3 and TYK2 kinases. In the test, the initial concentration of the crystal form I of compound LNK01004, Ruxolitinib, Tofacitinib and Upadacitinib for the detection of JAK1, JAK2, JAK3 and TYK2 kinases was 10 μM, and dilution was performed according to 3-fold gradient dilution, with a total of 10 concentrations. Duplicate wells were set for detecting, and the ATP concentration was 1 mM. The detection results are as shown in the table below:

| Half maximal inhibitory concentrations (IC50) of the crystal form I on activities of JAK1, JAK2, JAK3, and TYK2 kinases | | | | |
|---|---|---|---|---|
| IC50 (nM) | JAK1 (1 mM ATP) | JAK2 (1 mM ATP) | JAK3 (1 mM ATP) | TYK2 (1 mM ATP) |
| Crystal form I of LNK01004 | 10 | <0.51 | 275 | 1.0 |
| Ruxolitinib | 10 | 9.9 | 570 | 43 |
| Tofacitinib | 21 | 75 | 67 | 527 |
| Upadacitinib | 0.91 | 19 | 202 | 183 |

It can be seen from the test results that compared to Ruxolitinib, Tofacitinib and Upadacitinib, the crystal form I of the compound LNK01004 has the stronger inhibitory ability to activities of JAK1, JAK2, JAK3 and TYK2 kinases in the activity test, which shows that the crystal form I of LNK01004 has better pharmaceutical performance at the same concentration and the same dose.

Comparative Example 1 Preparation and
Characterization of Crystal Form II

About 50 mg of LNK01004 (as an amorphous form, prepared with reference to example 113 of CN 113227074 A) was weighed and completely dissolved at 50° C. by adding 2 ml of acetone/water (v:v=1:1), and the mixture was filtered with a 0.45 μm filter membrane to obtain a clear solution. The resulting clear solution was cooled to 5° C. at a cooling rate of 0.1° C./min. The resulting solid was collected by filtration to obtain the crystal form II. The crystal form II (sample number: FR00970-7-SC12) contained 0.3% acetone residue and had a water content of 12.2%. The crystal form II had a lower dehydration temperature of $T_{onset}$ 56.8° C., and was a metastable hydrate with high crystallinity.

Figure 8:
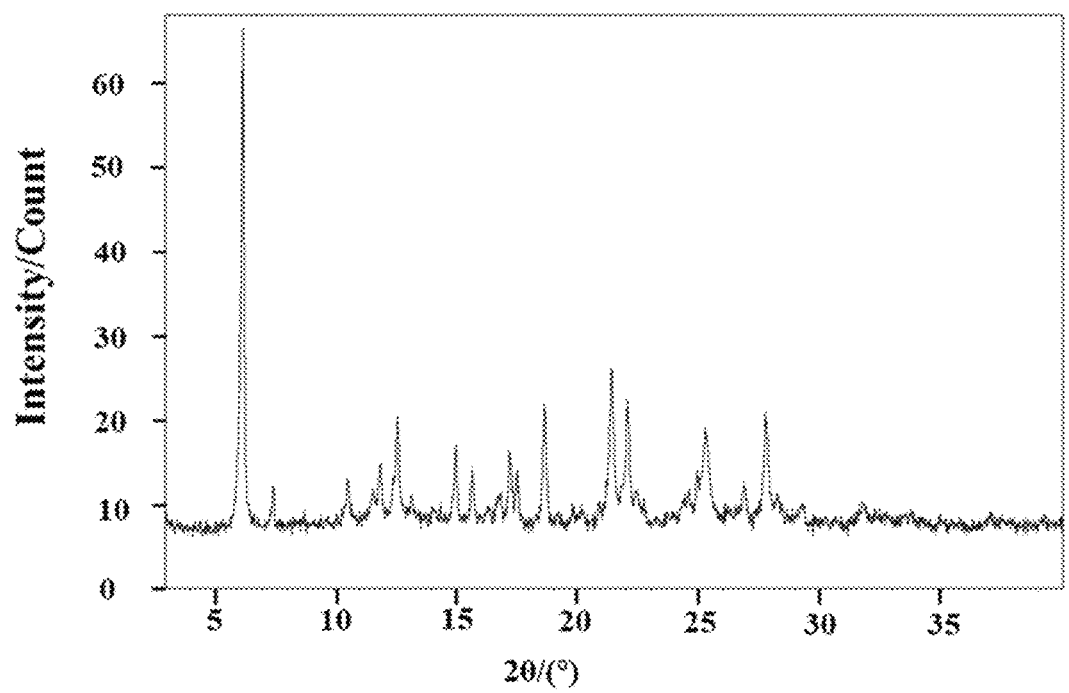
FIG. 8 is an XRPD pattern of the crystal form II.
Figure 9:
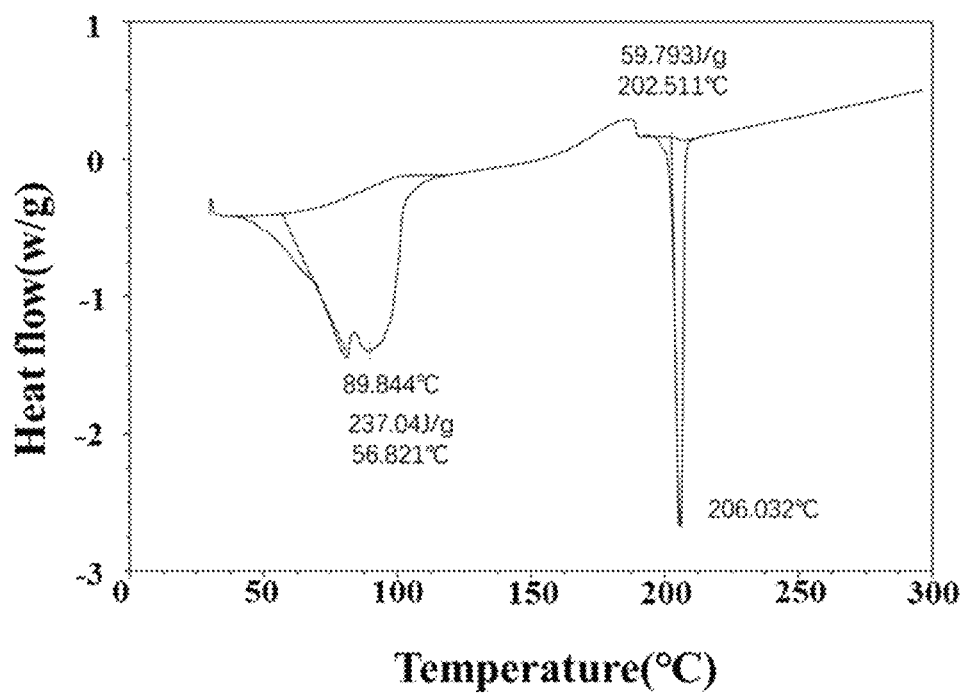
FIG. 9 is a DSC pattern of the crystal form II.
Figure 10:
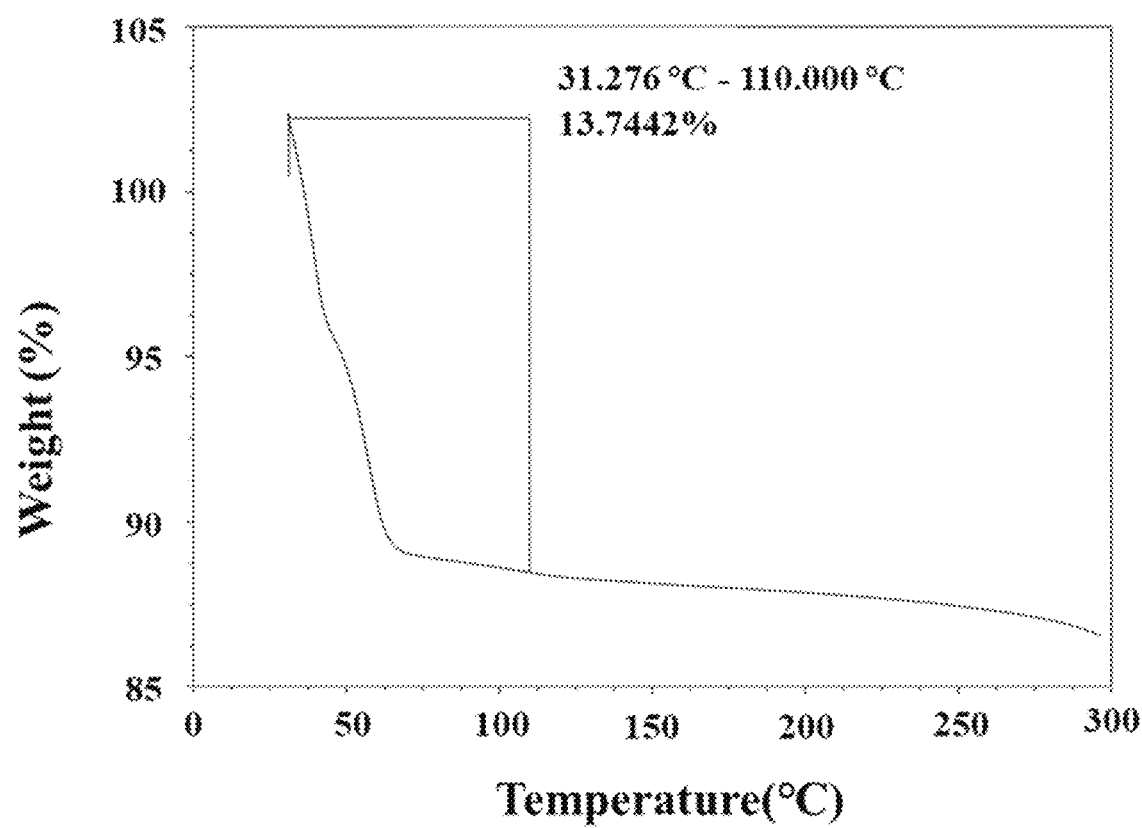
FIG. 10 is a TGA pattern of the crystal form II.
Figure 11:
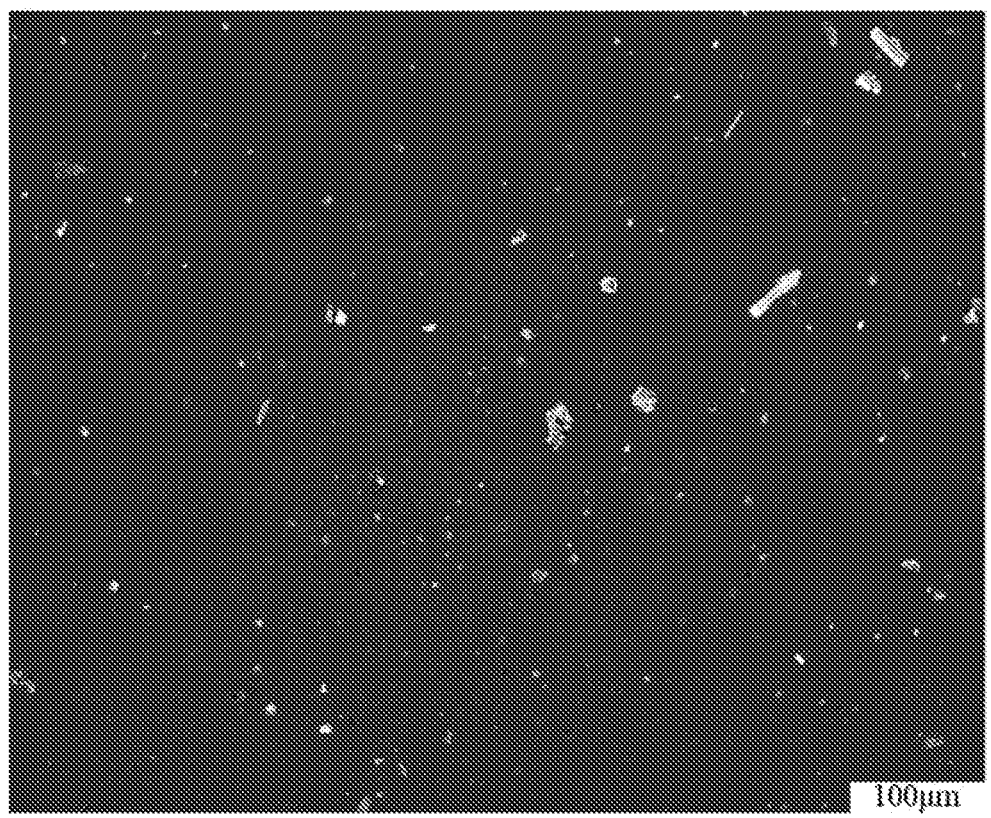
FIG. 11 is a PLM pattern of the crystal form II.

| Characterization data of crystal form II | | |
|---|---|---|
| Crystal form | Method | Crystal form II |
| Sample number | | FR00970-7-SC12 |
| Crystallinity | XRPD (FIG. 8) (2θ: 3° to 40°) | High crystallinity |
| Melting point and enthalpy of fusion | DSC (FIG. 9) (10° C./min) | |
| Thermal weight loss | TGA (FIG. 10) (10° C./min) | 13.6% @110° C. |
| Content of solvent | ¹H-NMR (DMSO-d6) | 0.06 equivalents of acetone (Theoretical residual solvent content of 0.3%) |
| Water assay | KF | 12.2% |
| Morphology | PLM (FIG. 11) | Columnar |

Comparative Example 2 Preparation and
Characterization of Crystal Form III

About 50 mg of LNK01004 (as an amorphous form, prepared with reference to example 113 of CN 113227074 A) was weighed and placed into a 2 mL glass bottle; 1 mL of methanol/dichloromethane (v:v=1:1) solvent was added; and the mixture was suspended at 400 rpm at 50° C. for one week. The resulting suspension was filtered, and the resulting solid part was characterized as the crystal form III. The crystal form III (sample number: FR00970-7-SC6) had no residual solvent, had a water content of 6.6%, and was a metastable hydrate with high crystallinity.

Figure 12:
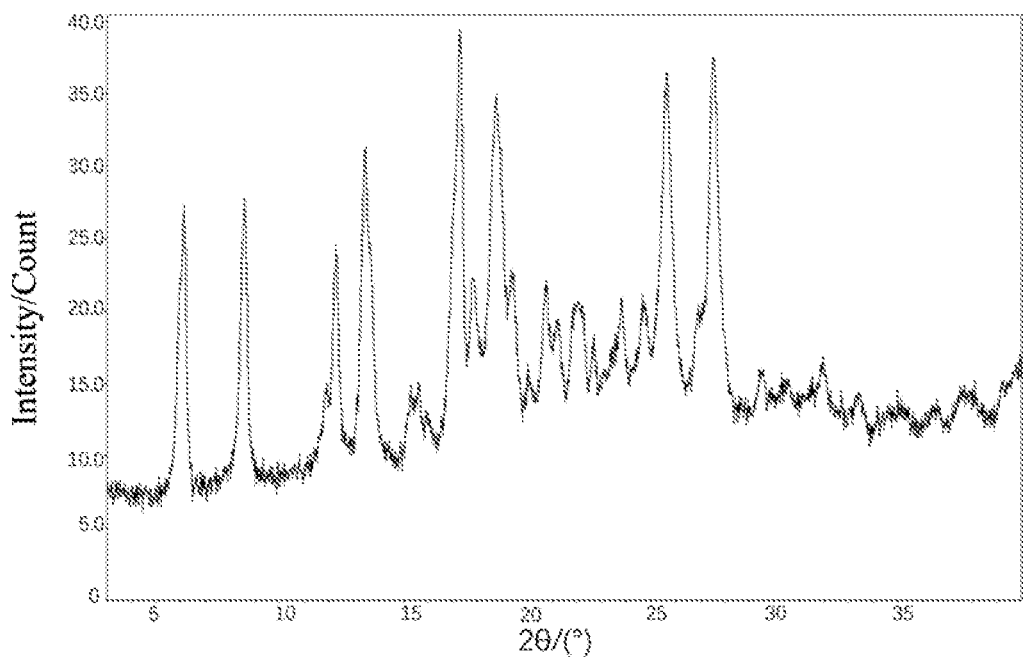
FIG. 12 is an XRPD pattern of the crystal form III.
Figure 13:
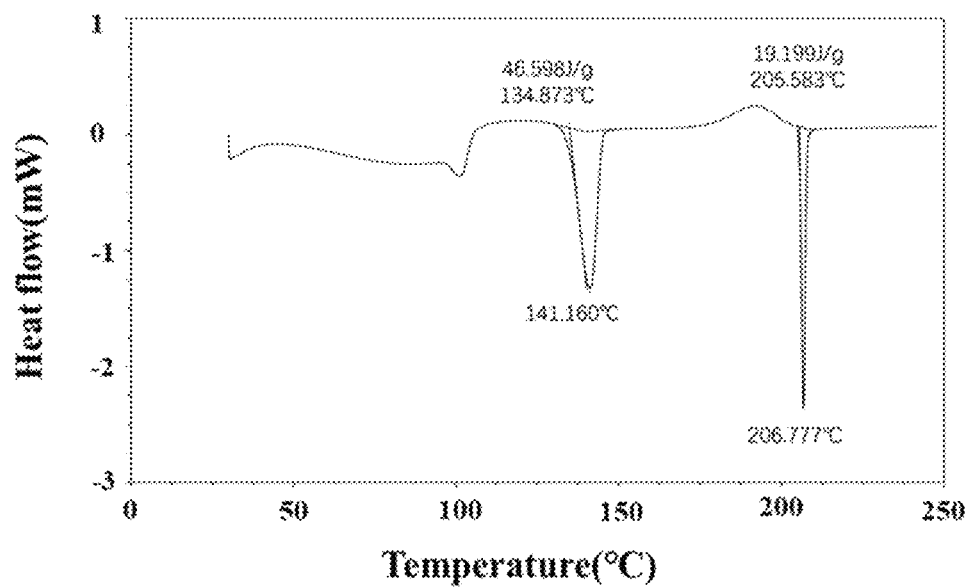
FIG. 13 is a DSC pattern of the crystal form III.
Figure 14:
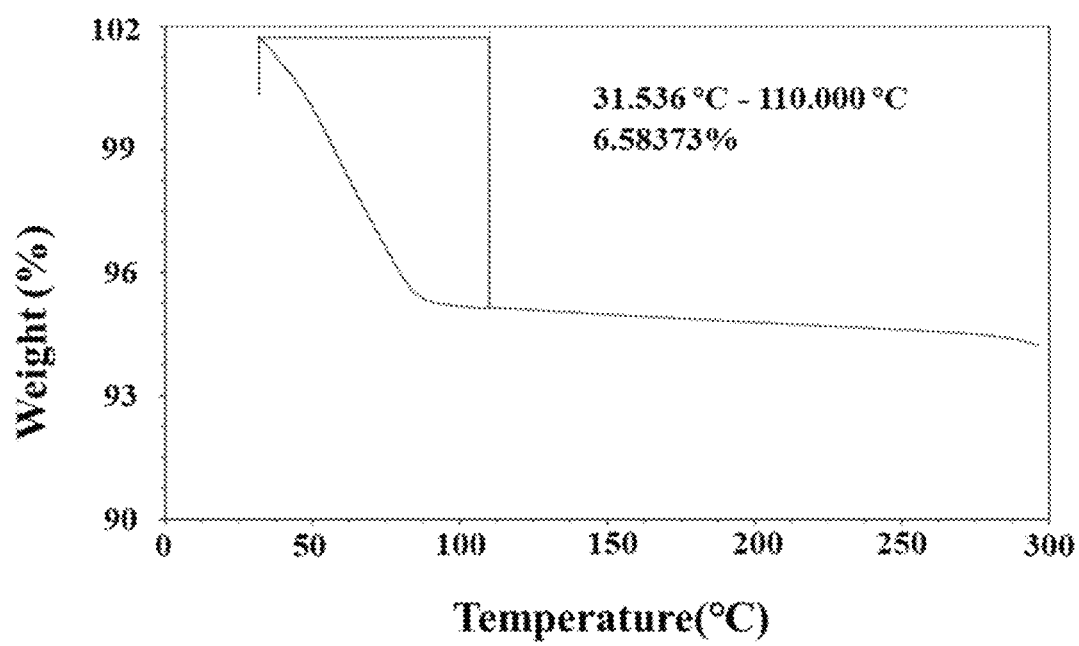
FIG. 14 is a TGA pattern of the crystal form III.
Figure 15:
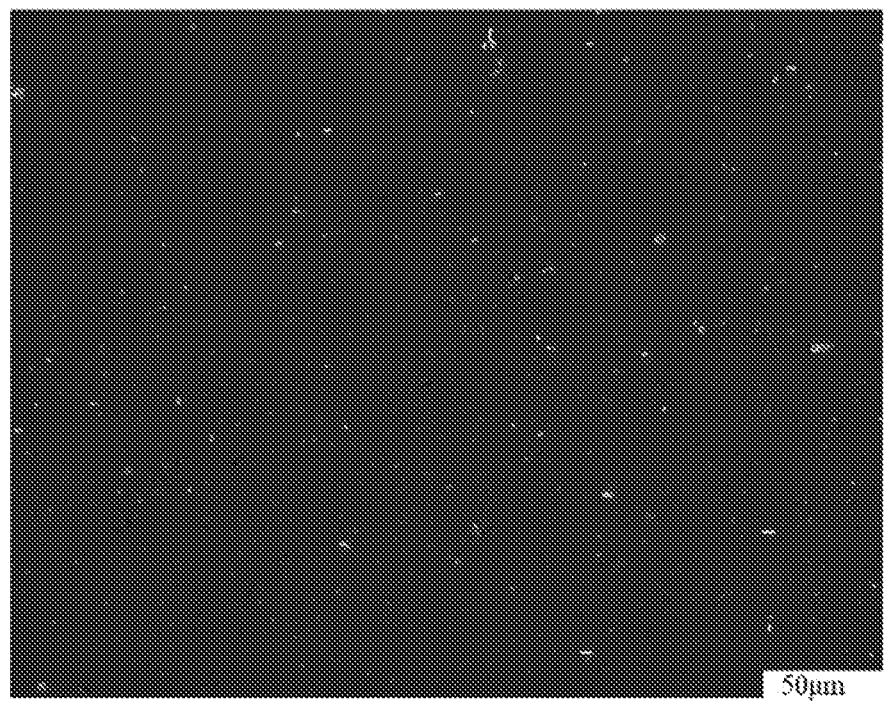
FIG. 15 is a PLM pattern of the crystal form III.

| Characterization data of crystal form III | | |
|---|---|---|
| Crystal form | Method | Crystal form III |
| Sample number | | FR00970-7-SC6 |
| Crystallinity | XRPD (FIG. 12) (2θ: 3° to 40°) | High crystallinity |
| Melting point and enthalpy of fusion | DSC (FIG. 13) (10° C./min) | |
| Thermal weight loss | TGA (FIG. 14) (10° C./min) | 6.6% @110° C. |
| Content of solvent | ¹H-NMR (DMSO-d6) | |
| Water assay | KF | 6.6% |
| Morphology | PLM (FIG. 15) | Blocky |

Comparative Example 3 Preparation and
Characterization of Crystal Form IV

Figure 24:
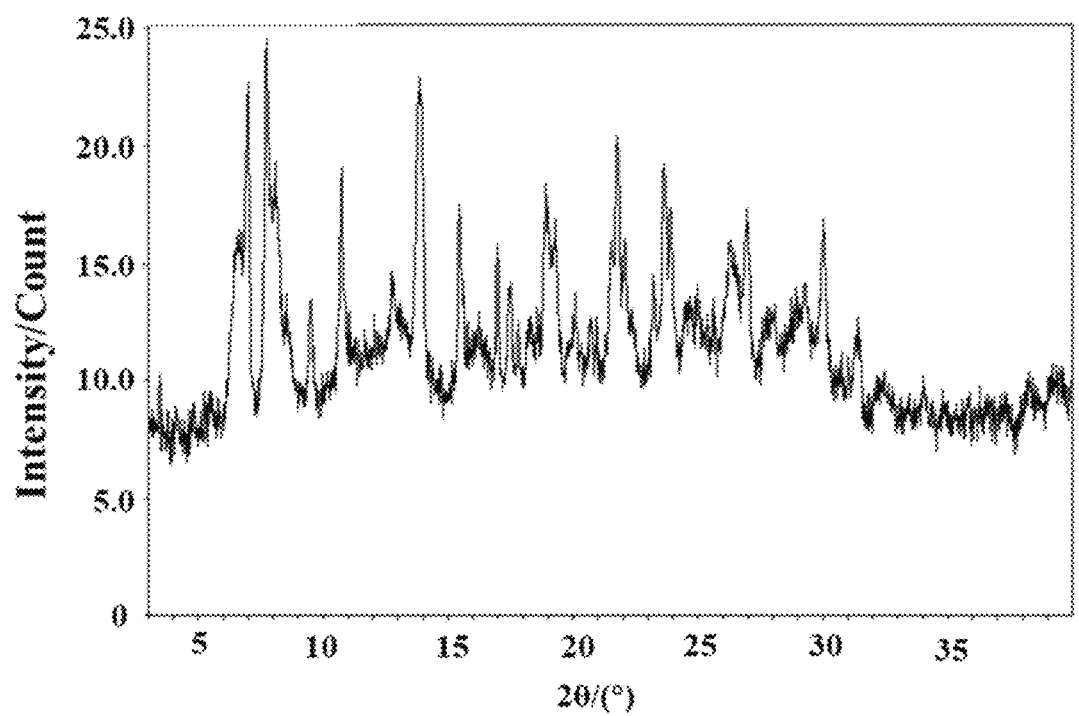
FIG. 24 is an XRPD pattern of the crystal form VI.

About 50 mg of LNK01004 (as an amorphous form, prepared with reference to example 113 of CN 113227074A) was weighed and placed into a 2 mL glass bottle; 1 mL of tetrahydrofuran/water (v:v=1:1) solvent was added and the mixture was suspended at 400 rpm at 25° C. for one week. The resulting suspension was filtered, and the resulting solid was characterized as the crystal form IV (FIG. 24). The crystal form IV (sample number: FR00970-12-SU3) contained 3% tetrahydrofuran residue and had a water content of 5.4%. After placed in the external environment (20-25° C., 80-95% RH) for 2 days, the crystal form IV was transformed into the crystal form VI. It shows that the crystal form IV is a metastable hydrate with high crystallinity.

Figure 16:
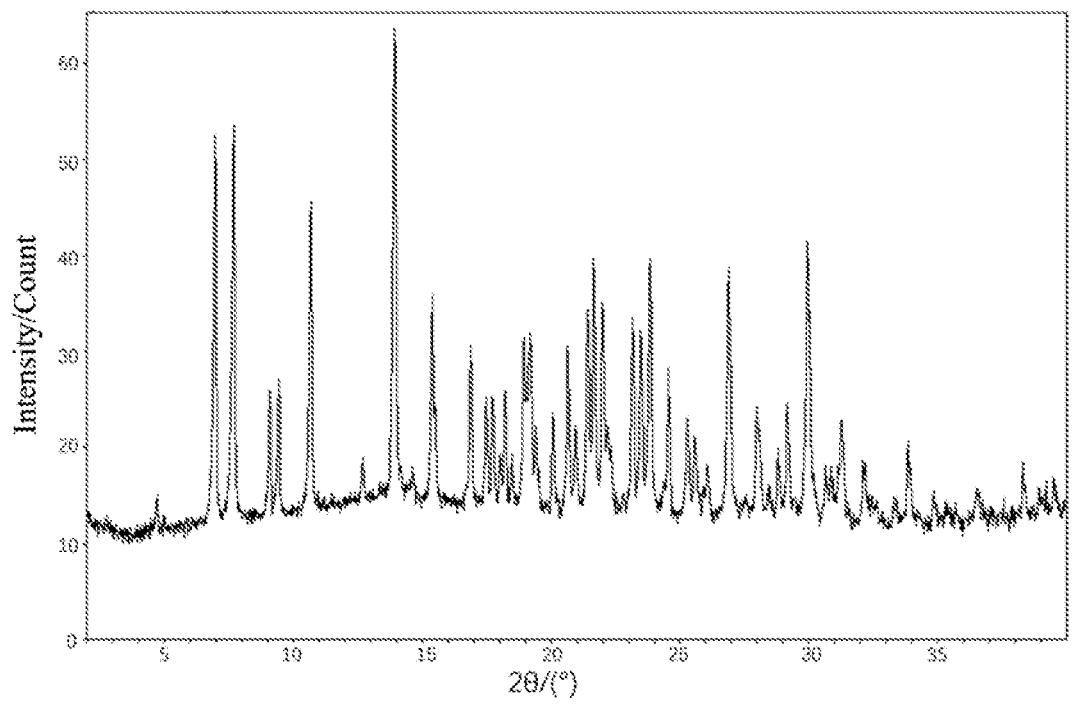
FIG. 16 is an XRPD pattern of the crystal form IV.

| Characterization data of crystal form IV | | |
|---|---|---|
| Crystal form | Method | Crystal form IV |
| Sample number | | FR00970-12-SU3 |
| Crystallinity | XRPD (FIG. 16) (2θ: 3° to 40°) | High crystallinity |

-continued

Figure 17:
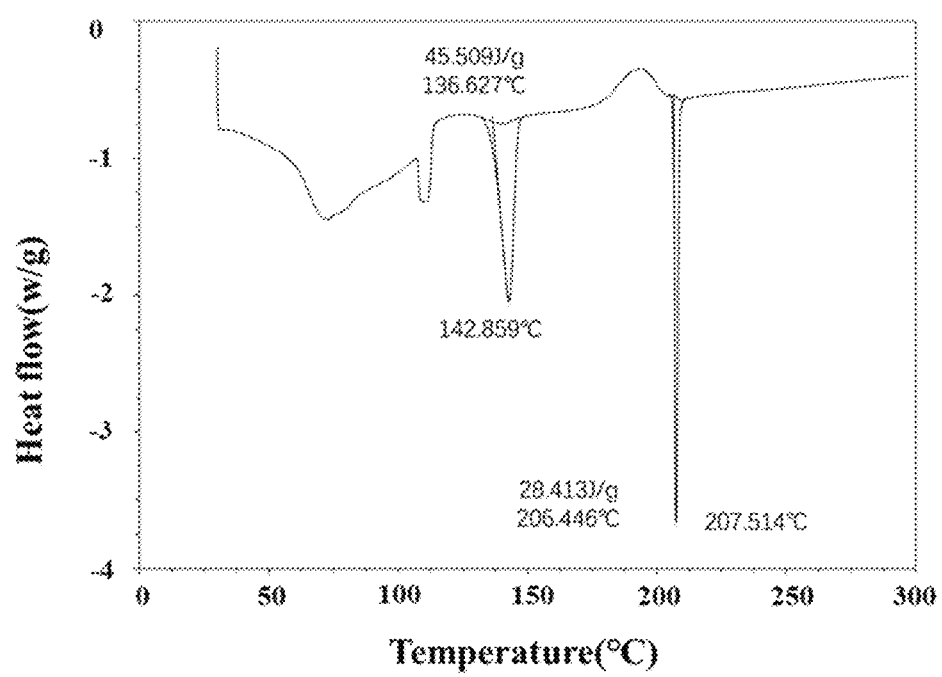
FIG. 17 is a DSC pattern of the crystal form IV.
Figure 18:
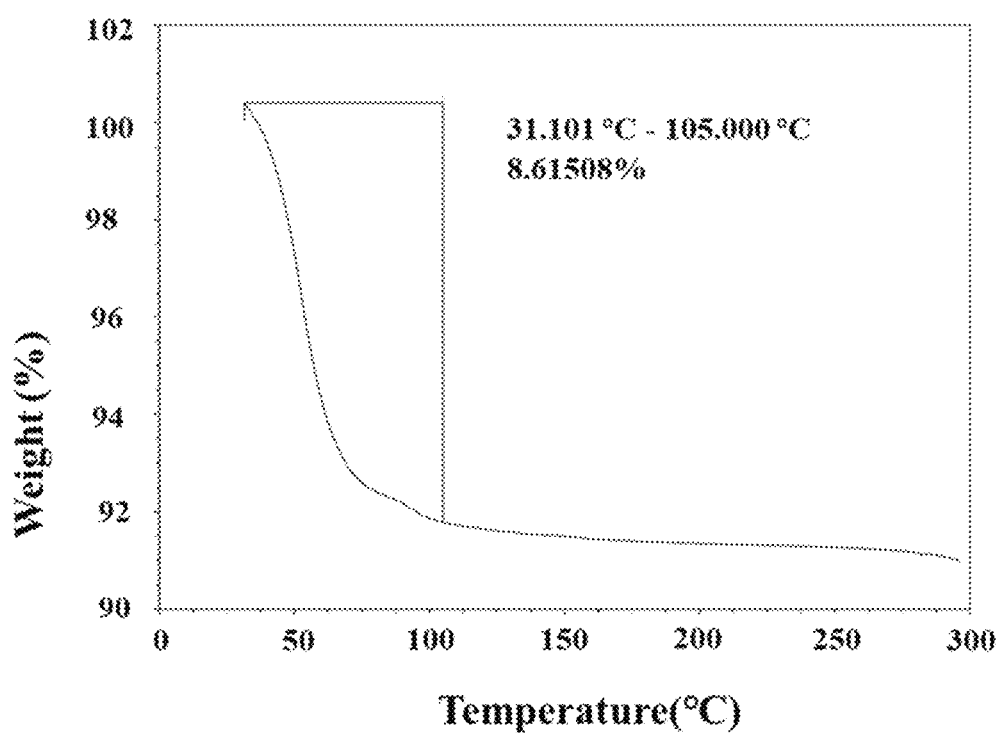
FIG. 18 is a TGA pattern of the crystal form IV.
Figure 19:
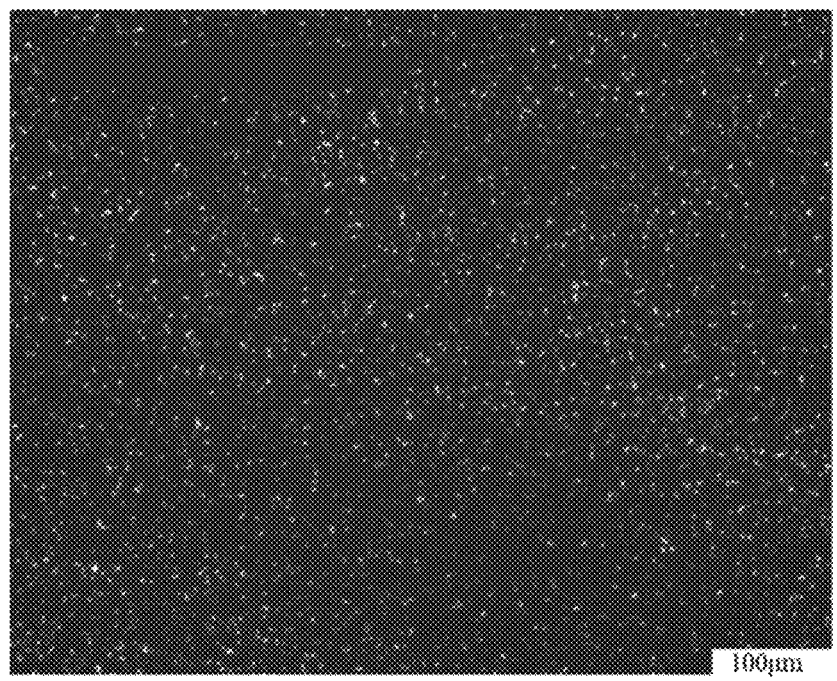
FIG. 19 is a PLM pattern of the crystal form IV.

| Characterization data of crystal form IV | | |
|---|---|---|
| Crystal form | Method | Crystal form IV |
| Melting point and enthalpy of fusion | DSC (FIG. 17) (10° C./min) | |
| Thermal weight loss | TGA (FIG. 18) (10° C./min) | 6.6% @110° C. |
| Content of solvent | $^1$H-NMR (DMSO-d6) | |
| Water assay | KF | 6.6% |
| Morphology | PLM (FIG. 19) | Blocky |

Comparative Example 4 Preparation and Characterization of Crystal Form V

About 20 mg of LNK01004 (as an amorphous form, prepared with reference to example 113 of CN 113227074 A) was weighed and completely dissolved by adding 1 ml of DMF/n-heptane (v:v=1:1) solvent, and the mixture was filtered with a 0.45 μm filter membrane to obtain a clear solution. The resulting clear solution was then placed at room temperature for evaporating slowly to obtain a solid as crystal form V. The crystal form V (sample number: FR00970-11-VD3) contained 1.6 equivalents of DMF. After heated to 150° C. to remove the solvent, the crystal form V was transformed to the crystal form I (the XRPD data of which were consistent with those of Crystal form I Preparation example 1).

Figure 20:
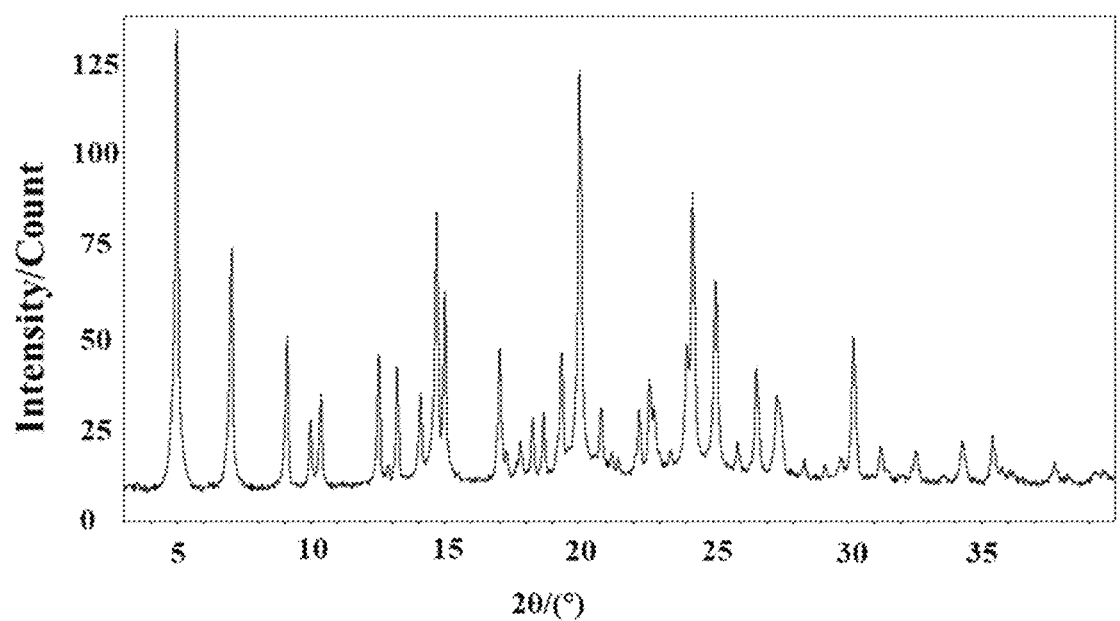
FIG. 20 is an XRPD pattern of the crystal form V.
Figure 21:
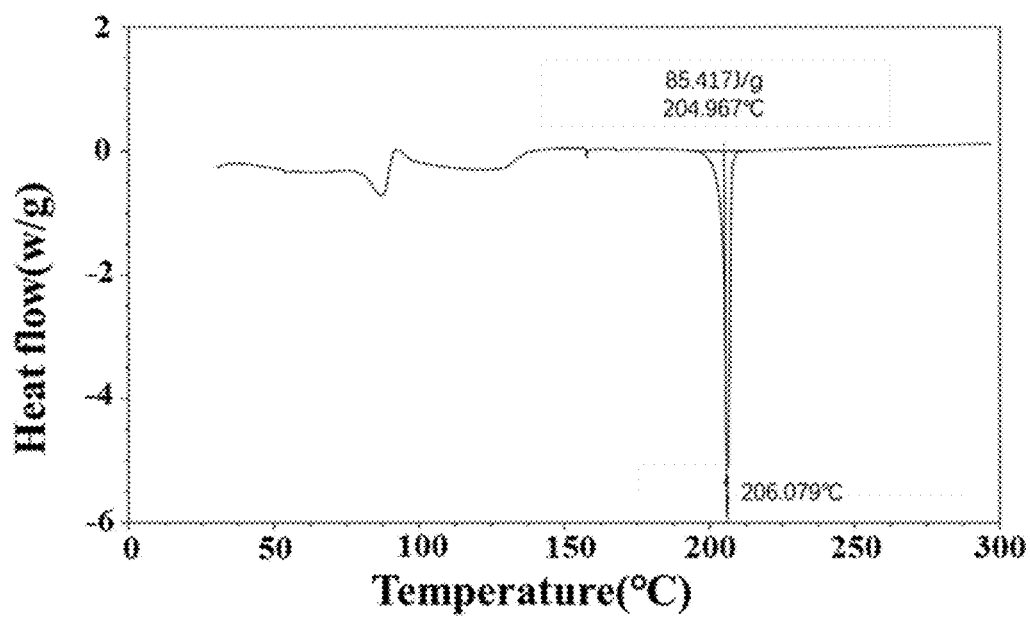
FIG. 21 is a DSC pattern of the crystal form V.
Figure 22:
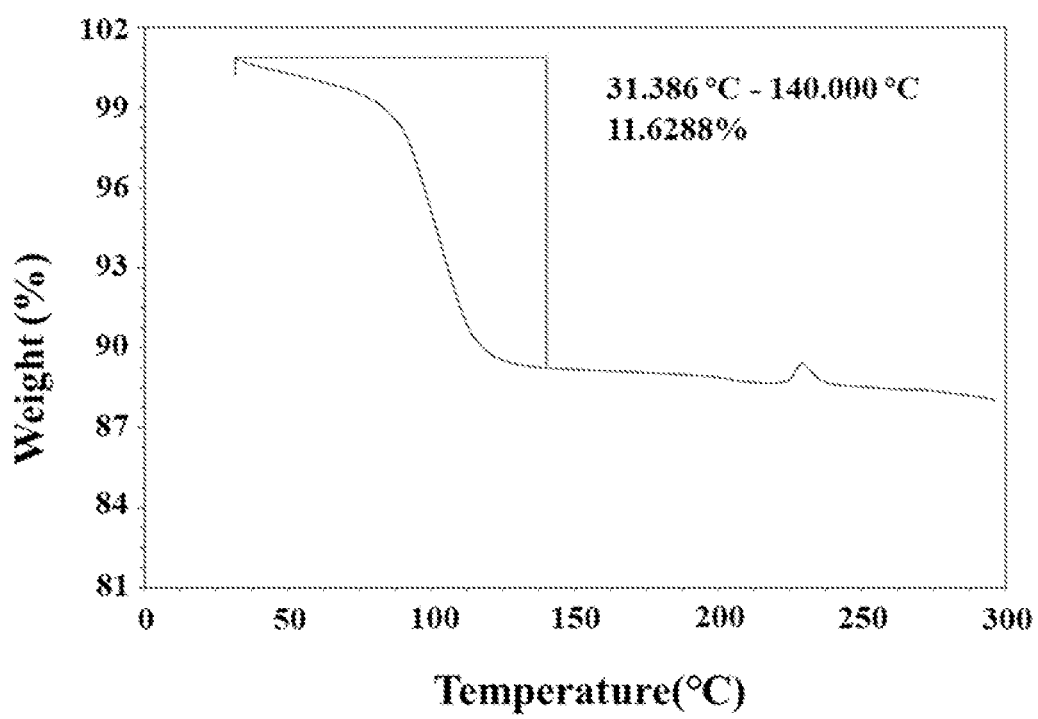
FIG. 22 is a TGA pattern of the crystal form V.
Figure 23:
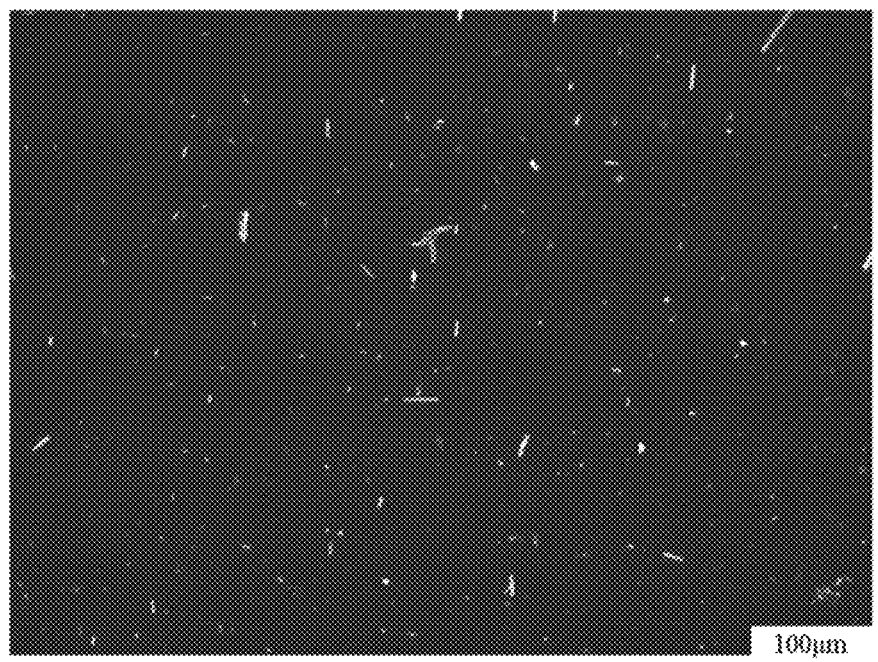
FIG. 23 is a PLM pattern of the crystal form V.

| Characterization data of crystal form V | | |
|---|---|---|
| Crystal form | Method | Crystal form V |
| Sample number | | FR00970-11-VD3 |
| Crystallinity | XRPD (FIG. 20) (2θ: 3° to 40°) | High crystallinity |
| Melting point and enthalpy of fusion | DSC (FIG. 21) (10° C./min) | 205.0° C.; 85 J/g |
| Thermal weight loss | TGA (FIG. 22) (10° C./min) | 11.6% @140° C. |
| Content of solvent | $^1$H-NMR (DMSO-d6) | 1.6 equivalents of DMF (Theoretical residual solvent content of 20%) |
| Water assay | KF | / |
| Morphology | PLM (FIG. 23) | Blocky |

"/": indicates not performing.

Comparative Example 5 Preparation and Characterization of Crystal Form VI

About 50 mg of LNK01004 (as an amorphous form, prepared with reference to example 113 of CN 113227074 A) was weighed and placed into a 2 mL glass bottle; 1 mL of tetrahydrofuran/water (v:v=1:1) solvent was added and the mixture was suspended at 400 rpm at 25° C. for one week. The resulting suspension was filtered; The resulting solid was characterized as the crystal form IV; After placed in the external environment (20 to 25° C., 80 to 95% RH) for 2 days, the crystal form IV was transformed into the crystal form VI. The crystal form VI (sample number: FR00970-9-TC17) contained 2.3% THF residue and had a water content of 4.8%. The crystal form VI was unstable and transformed into other crystal forms under certain conditions. The crystal form VI was transformed into the crystal form VII when being exposed to 0 humidity, and transformed into the crystal form III when being heated to 120° C. and then cooled to room temperature.

Figure 25:
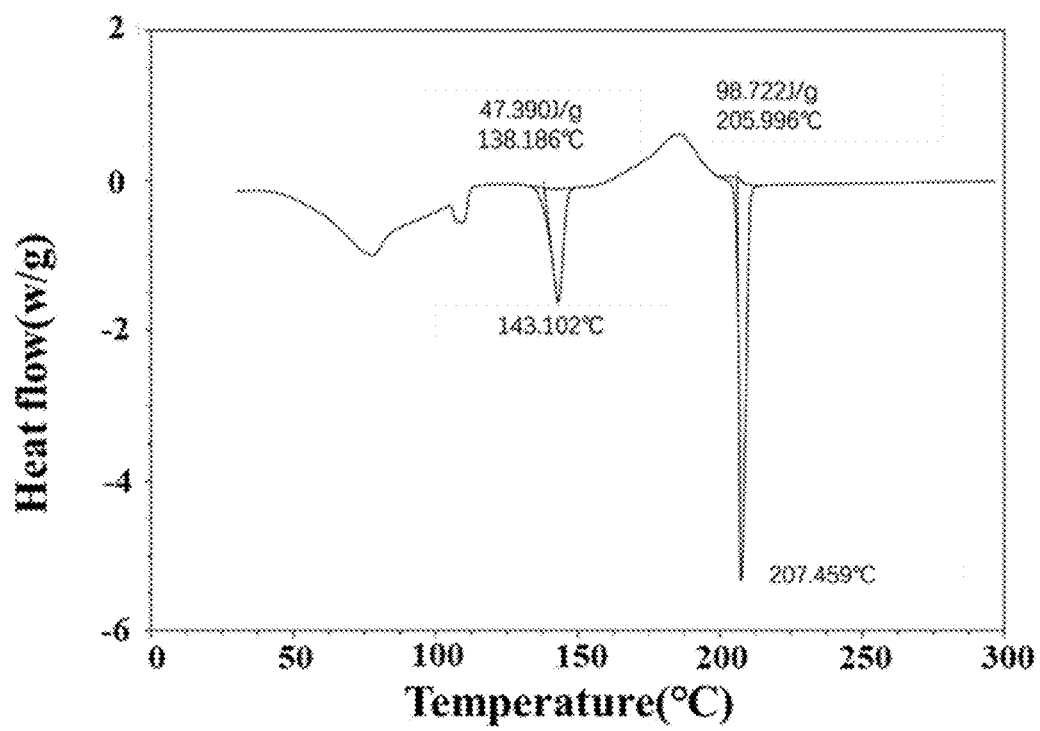
FIG. 25 is a DSC pattern of the crystal form VI.
Figure 26:
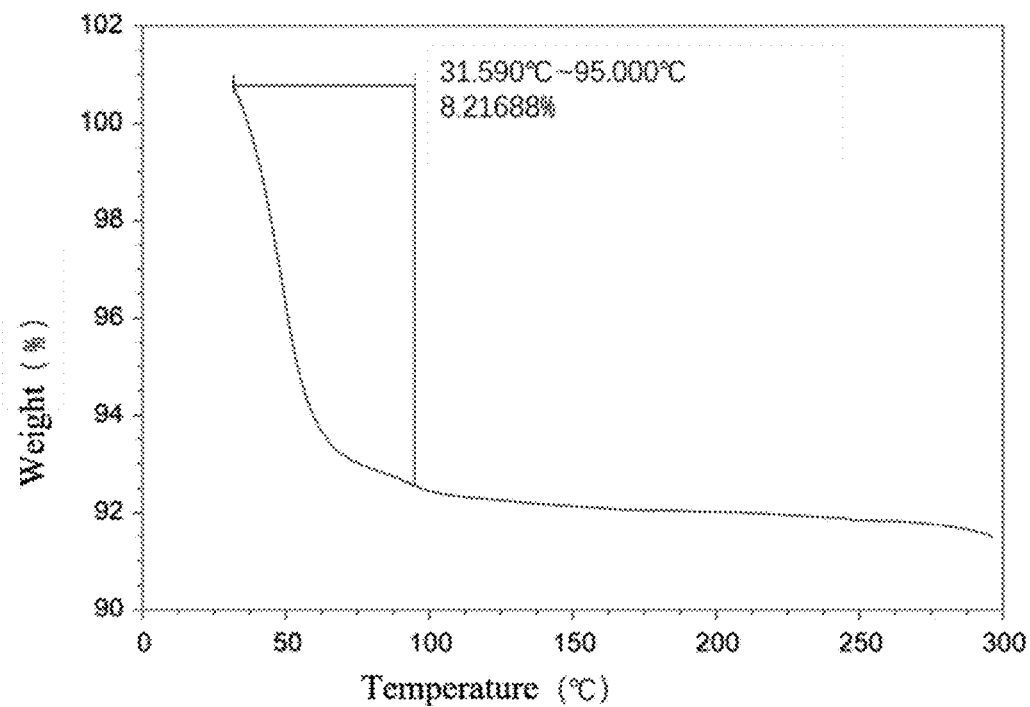
FIG. 26 is a TGA pattern of the crystal form VI.
Figure 27:
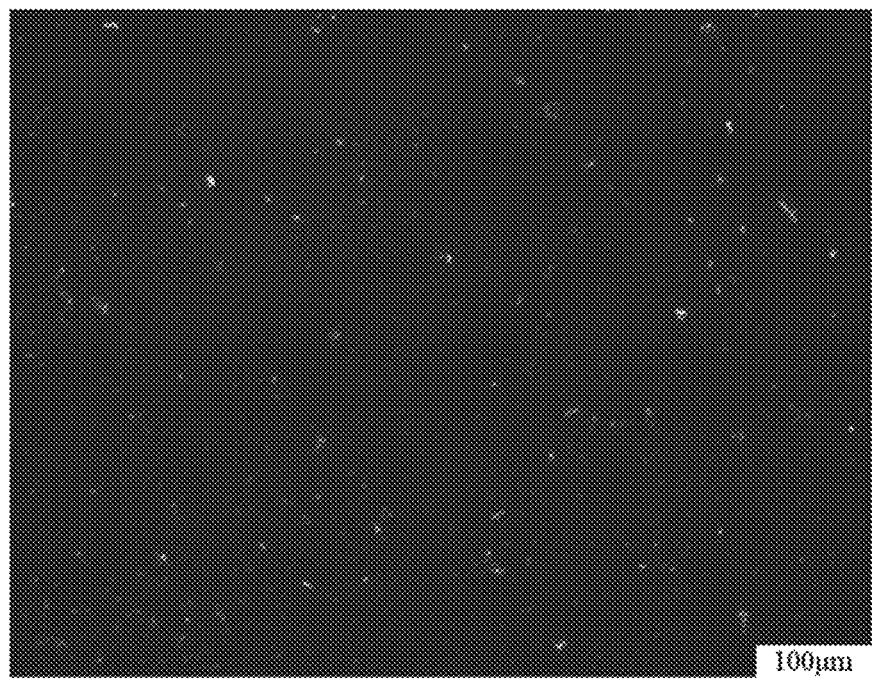
FIG. 27 is a PLM pattern of the crystal form VI.

| Characterization data of crystal form VI | | |
|---|---|---|
| Crystal form | Method | Crystal form VI |
| Sample number | | FR00970-9-TC17 |
| Crystallinity | XRPD (FIG. 24) (2θ: 3° to 40°) | Medium crystallinity |
| Melting point and enthalpy of fusion | DSC (FIG. 25) (10° C./min) | |
| Thermal weight loss | TGA (FIG. 26) (10° C./min) | 8.2% @95° C. |
| Content of solvent | $^1$H-NMR (DMSO-d6) | 0.16 equivalents of tetrahydrofuran (Theoretical residual solvent content of 2.3%) |
| Water content | KF | 4.8% |
| Morphology | PLM (FIG. 27) | Blocky |

Comparative Example 6 Preparation and Characterization of Crystal Form VII

About 50 mg of LNK01004 (as an amorphous form, prepared with reference to example 113 of CN 113227074 A) was weighed and placed into a 2 mL glass bottle; 1 mL of tetrahydrofuran/water (v:v=1:1) solvent was added and the mixture was suspended at 400 rpm at 25° C. for one week. The resulting suspension was filtered and the resulting solid was characterized as the crystal form IV; After equilibrated at 0% RH for 12 h, the crystal form IV was transformed into the crystal form VII. The crystal form VII was stable only at low RH, and the crystal form VII was transformed into the crystal form III within 2 h under a condition of 60% RH. The crystal form VII and the crystal form III had similar XRPD patterns, except that the positions of several peaks were slightly shifted.

Comparative Example 7 Preparation and Characterization of Amorphous Form

About 50 mg of LNK01004 (as an amorphous form, prepared with reference to example 113 of CN 113227074 A) was weighed and placed into a 2 mL glass bottle and completely dissolved at 50° C. by adding 1 mL of acetonitrile/water (v:v=1:1) solvent, and the mixture was filtered with a 0.45 μm filter membrane to obtain a clear solution. The resulting clear solution was cooled to 5° C. at a cooling rate of 0.1° C./min. The resulting solid was collected by filtration to obtain an amorphous form (sample number: FR00970-7-SC8). It was found from the crystal form of DSC heating study (heating from 30° C. to melting at a rate of 10° C./min; cooling from melting to −20° C. at a rate of 20° C./min) that for the amorphous form at 30° C. to 110° C., the solvent was removed and for heating to 140° C. to 190° C., the amorphous form was transformed into the crystal form I (the characterization data of which were identical to those of "Crystal form I Preparation and characterization example 1").

Figure 28:
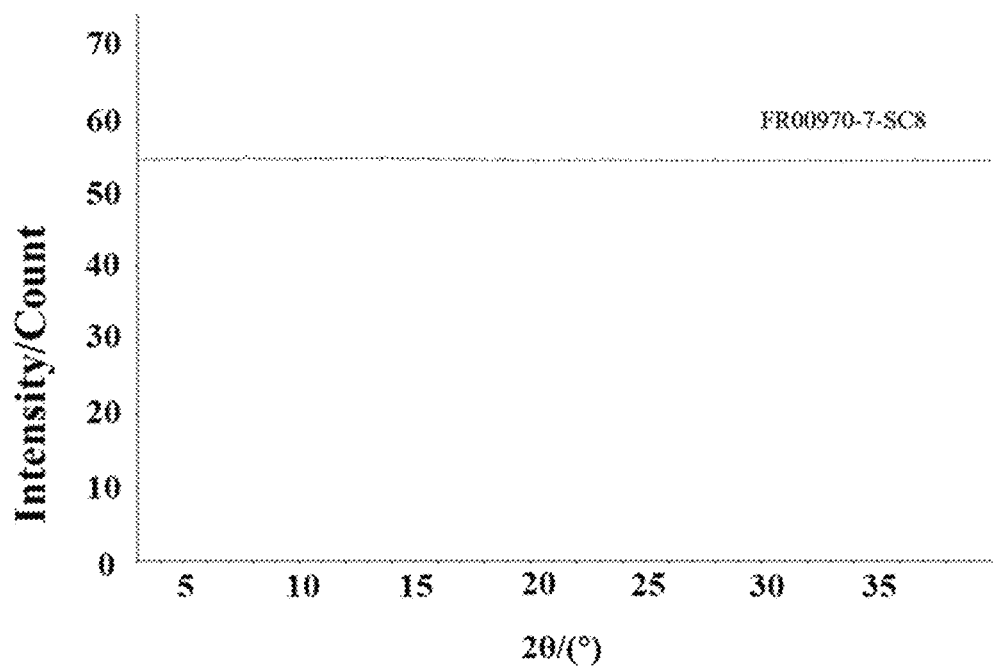
FIG. 28 is an XRPD pattern of the amorphous form.
Figure 29:
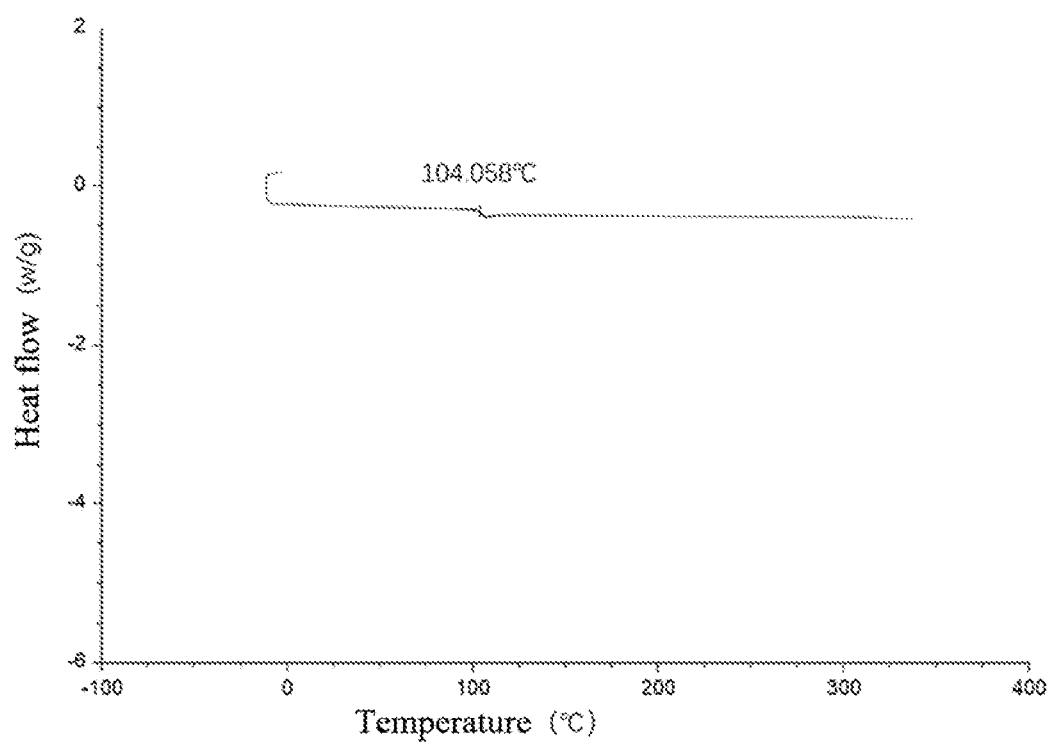
FIG. 29 is a DSC pattern of the amorphous form.

| Characterization data of crystal form in an amorphous form | | |
| --- | --- | --- |
| Crystal form | Method | Amorphous form |
| Sample number | | FR00970-7-SC8 |
| Crystallinity | XRPD (FIG. 28) (2θ: 3° to 40°) | Amorphous form |
| Melting point and enthalpy of fusion | DSC (FIG. 29) (10° C./min) | The amorphous form has a glass transition temperature of 104° C. |
| Crystal form transformation by DSC heating | DSC (10° C./min) | For the amorphous form at 3° C. to 110° C., the solvent was removed; At 140° C. to 190° C., the amorphous form was transformed into the crystal form I. |

Although the specific embodiments of the present disclosure have been described above, it will be understood by those of skill in the art that these are merely illustrative, and that various alterations or modifications can be made to these embodiments without departing from the principle and essence of the present disclosure. Therefore, the scope of protection of the present disclosure is defined by the appended claims.

What is claimed is:

1. A crystal form I of compound 1, wherein the crystal form I has an X-ray powder diffraction pattern comprising diffraction peaks at the following positions: 8.60°±0.2°, 10.25°±0.2°, 11.96°±0.2°, 14.35°±0.2°, 15.39°±0.2° 16.59°±0.2°, 17.06°±0.2°, and 18.16°±0.2° 2θ, as determined by using Cu—Kα radiation;

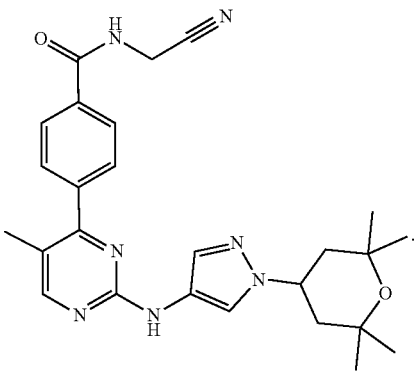

2. The crystal form I according to claim 1, wherein the crystal form I meets one or more of the following conditions:
   (1) the crystal form I has an X-ray powder diffraction pattern further comprising diffraction peaks at one or more of the following positions: 12.77°±0.2°, 13.48°±0.2°, 14.04°±0.2°, 17.27°±0.2°, 18.83°±0.2°, 20.52°±0.2°, 20.77°±0.2°, 21.45°±0.2°, 22.12°±0.2°, 22.79°±0.2°, 23.55°±0.2°, 24.04°±0.2°, 24.40°±0.2°, 25.08°±0.2°, 25.87°±0.2°, 26.51°±0.2°, 26.73°±0.2°, 26.89°±0.2°, 27.36°±0.2°, and 28.29°±0.2° 2θ;
   (2) the crystal form I has a differential scanning calorimetry pattern comprising an endothermic peak at 207.4° C. to 209.2° C.;
   (3) the crystal form I has a thermogravimetric analysis pattern comprising a weight loss of 0.0% at 30.07° C. to 208.96° C.

3. The crystal form I according to claim 2, wherein the crystal form I has an X-ray powder diffraction pattern further comprising diffraction peaks at one or more of the following positions: 28.93°±0.2°, 29.42°±0.2°, 30.63°±0.2°, 33.00°±0.2°, 33.37°±0.2°, 34.43°±0.2°, and 37.09°±0.2° 2θ.

4. The crystal form I according to claim 2, wherein the crystal form I meets one or more of the following conditions:
   (1) the crystal form I has an X-ray powder diffraction pattern at 2θ comprising diffraction peaks as shown in the table below:

| Diffraction angle [° 2θ] | d value [Å] | Relative intensity [%] |
| --- | --- | --- |
| 8.599 | 10.27532 | 94.0 |
| 10.250 | 8.62286 | 41.5 |
| 11.957 | 7.39559 | 80.8 |
| 12.774 | 6.92428 | 14.1 |
| 13.482 | 6.56235 | 13.1 |
| 14.043 | 6.30159 | 52.8 |
| 14.345 | 6.16938 | 33.9 |
| 15.392 | 5.75198 | 16.1 |
| 16.594 | 5.33787 | 18.7 |
| 17.063 | 5.19224 | 56.9 |
| 17.270 | 5.13049 | 27.3 |
| 18.156 | 4.88225 | 100.0 |
| 18.830 | 4.70888 | 6.0 |
| 20.523 | 4.32402 | 26.0 |
| 20.765 | 4.27428 | 10.0 |
| 21.446 | 4.14001 | 43.6 |
| 22.118 | 4.01569 | 17.0 |
| 22.792 | 3.89842 | 5.7 |
| 23.545 | 3.77553 | 10.5 |
| 24.043 | 3.69847 | 13.5 |
| 24.406 | 3.64422 | 33.5 |
| 25.081 | 3.54761 | 20.4 |
| 25.868 | 3.44150 | 2.8 |
| 26.508 | 3.35979 | 2.8 |
| 26.732 | 3.33219 | 5.4 |
| 26.889 | 3.31302 | 9.2 |
| 27.360 | 3.25704 | 10.2 |
| 28.285 | 3.15261 | 6.9 |
| 28.930 | 3.08383 | 30.2 |
| 29.419 | 3.03366 | 5.0 |
| 30.630 | 2.91642 | 3.4 |
| 33.000 | 2.71216 | 3.7 |
| 33.370 | 2.68298 | 2.6 |
| 34.429 | 2.60282 | 2.2 |
| 37.089 | 2.42198 | 2.0 |

Figure 3:
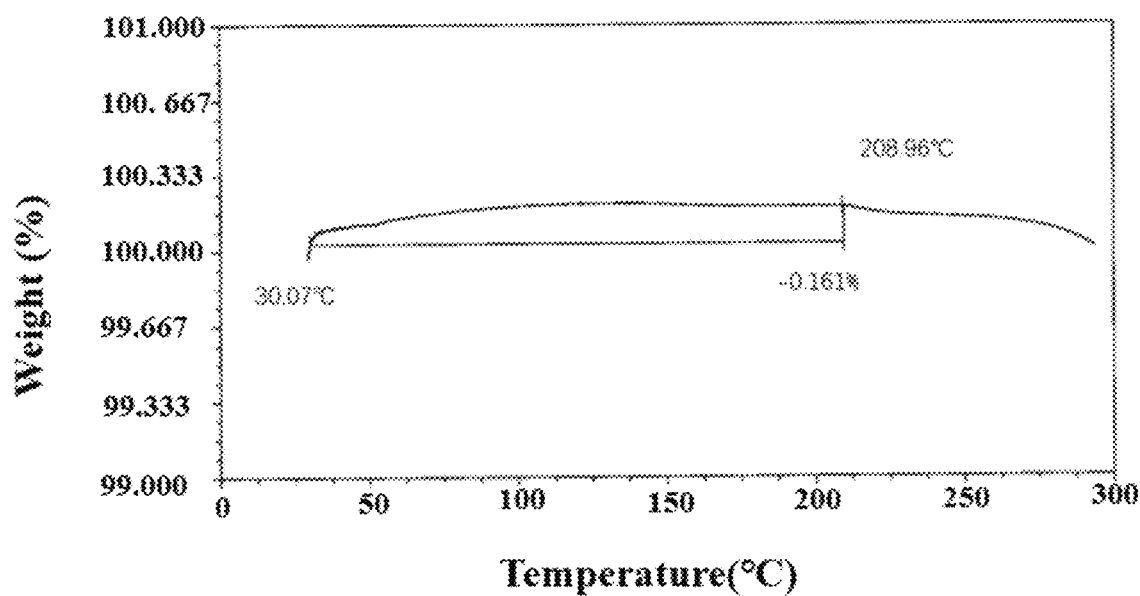
FIG. 3 is a TGA pattern of the crystal form I.

(2) the crystal form I has a differential scanning calorimetry pattern comprising an endothermic peak at 207.4° C. to 209.2° C., with a heat of fusion of 123.76 J/g;
   (3) the crystal form I has a thermogravimetric analysis pattern as shown in FIG. 3.

5. The crystal form I according to claim 4, wherein the crystal form I meets one or more of the following conditions:
   (1) the crystal form I has an X-ray powder diffraction pattern at 2θ shown in FIG. 1;
   (2) the crystal form I has a differential scanning calorimetry pattern shown in FIG. 2.

6. A preparation method for the crystal form I according to claim 1, wherein the preparation method comprises scheme 1 or scheme 2; wherein
   the scheme 1 comprises the following sequential operations: at 40° C., adding methanol to a solution of the compound 1 and tetrahydrofuran, concentrating the obtained solution, adding methanol again to the concentrated solution, and stirring for crystallization to obtain the crystal form I;

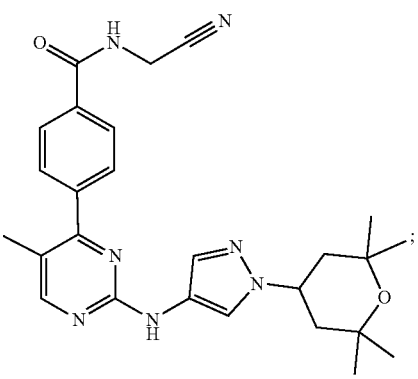

the scheme 2 comprises a step of cooling a solution of the compound 1 in tetrahydrofuran/methanol and isopropanol to obtain the crystal form I.

7. The preparation method for the crystal form I according to claim 6, wherein the preparation method meets one or more of the following conditions:
   (1) the scheme 1 further comprises the following post-processing steps: filtering, washing, drying under reduced pressure, and sieving to obtain the crystal form I;
   (2) in the scheme 2, the mass ratio of the compound 1 to tetrahydrofuran/methanol is (1:3) to (1:5);
   (3) in the scheme 2, regarding the tetrahydrofuran/methanol, the mass ratio of tetrahydrofuran to methanol is (2:1) to (1:2);
   (4) in the scheme 2, the mass ratio of the compound 1 to isopropanol is (1:11) to (1:13);
   (5) in the scheme 2, the temperature at which the compound 1 is dissolved in tetrahydrofuran/methanol and isopropanol is 50° C. to 60° C.;
   (6) in the scheme 2, the cooling lowers the temperature to 0° C. to 5° C.;
   (7) in the scheme 2, a temperature-holding time after the cooling is 15 to 30 h; and
   (8) the scheme 2 further comprises the following post-processing steps: filtering, washing, drying under reduced pressure, and sieving to obtain the crystal form I.

8. The preparation method for the crystal form I according to claim 7, wherein the preparation method meets one or more of the following conditions:
   (1) in the scheme 2, the mass ratio of the compound 1 to tetrahydrofuran/methanol is 1:4;
   (2) in the scheme 2, regarding the tetrahydrofuran/methanol, the mass ratio of tetrahydrofuran to methanol is 1:1;
   (3) in the scheme 2, the mass ratio of the compound 1 to isopropanol is 1:12;
   (4) in the scheme 2, the temperature at which the compound 1 is dissolved in tetrahydrofuran/methanol and isopropanol is 55° C.;
   (5) in the scheme 2, the cooling lowers the temperature to 0° C.; and
   (6) in the scheme 2, a temperature-holding time after the cooling is 24 h.

9. The preparation method for the crystal form I according to claim 7, wherein the scheme 1 comprises the following sequential operations: at 40° C., adding methanol to a solution of the compound 1 and tetrahydrofuran, concentrating the obtained solution, adding methanol again to the concentrated solution, and stirring for crystallization to obtain the crystal form I,
   wherein a temperature at which the compound 1 is dissolved in the tetrahydrofuran to form the solution of the compound 1 and tetrahydrofuran is 50° C. to 60° C.;
   or, the mass ratio of the compound 1 to the tetrahydrofuran is (1:8) to (1:9);
   or, the mass ratio of the compound 1 to the methanol added for the first time is (1:16) to (1:18);
   or, the mass of the concentrated solution is 4 to 6 times of the mass of the compound 1;
   or, the mass ratio of the compound 1 to the methanol added for the second time is (1:2) to (1:3).

10. The preparation method for the crystal form I according to claim 9, wherein the mass ratio of the compound 1 to the tetrahydrofuran is 1:8.7;
   or, the mass ratio of the compound 1 to the methanol added for the first time is 1:17;
   or, the mass of the concentrated solution is 5 times of the mass of the compound 1;
   or, the mass ratio of the compound 1 to the methanol added for the second time is 1:2.3.

11. The preparation method for the crystal form I according to claim 7, wherein the scheme 2 comprises the following operations: warming the compound 1 and tetrahydrofuran/methanol, adding isopropanol to dissolve the compound 1, adding isopropanol again, and cooling to form a suspension to obtain the crystal form I.

12. A pharmaceutical composition, comprising the crystal form I according to claim 1 and a pharmaceutical excipient.

13. A method for treating or preventing a disease related to JAK kinases in a subject in need thereof, comprising: administering the crystal form I according to claim 1 to the subject, wherein
   the disease related to JAK kinases is inflammatory bowel disease, psoriasis, vitiligo, atopic dermatitis, systemic lupus erythematosus, asthma, diabetic nephropathy, chronic myelogenous leukemia, essential thrombocythemia, polycythemia vera, myelofibrosis, breast cancer or ovarian cancer.

\* \* \* \* \*